(12) United States Patent
Mehta et al.

(10) Patent No.: US 11,446,424 B2
(45) Date of Patent: Sep. 20, 2022

(54) SYSTEMS AND METHODS FOR MEASURING FLUID FLOW IN A VENTURI BASED SYSTEM

(71) Applicant: JOHNSON & JOHNSON SURGICAL VISION, INC., Santa Ana, CA (US)

(72) Inventors: Deep Mehta, Irvine, CA (US); Dung T. Ma, Anaheim, CA (US); Sandra H. Keh, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 294 days.

(21) Appl. No.: 16/152,312

(22) Filed: Oct. 4, 2018

(65) Prior Publication Data

US 2019/0099529 A1    Apr. 4, 2019

Related U.S. Application Data

(60) Provisional application No. 62/568,174, filed on Oct. 4, 2017.

(51) Int. Cl.
*A61M 1/00* (2006.01)
*A61M 3/02* (2006.01)
*A61F 9/007* (2006.01)

(52) U.S. Cl.
CPC .......... *A61M 1/74* (2021.05); *A61F 9/00736* (2013.01); *A61F 9/00745* (2013.01);
(Continued)

(58) Field of Classification Search
CPC .............. A61M 1/0031; A61M 1/0029; A61M 1/0058; A61M 1/0076; A61M 3/0216; A61F 9/00736; A61F 9/00745

See application file for complete search history.

(56) References Cited

U.S. PATENT DOCUMENTS 3,393,566 A * 7/1968 Green .................. G01L 9/0052
73/727
3,575,301 A   4/1971 Panissidi
(Continued)

FOREIGN PATENT DOCUMENTS

CN    110338970 A    10/2019
DE    19753636 A1    9/1999
(Continued)

OTHER PUBLICATIONS

International Search Report and Written Opinion for Application No. PCT/IB2018/057494, dated Dec. 19, 2018, 13 pages.
(Continued)

*Primary Examiner* — Dung T Ulsh
(74) *Attorney, Agent, or Firm* — Johnson & Johnson Surgical Vision, Inc.

(57) ABSTRACT

Variables of a surgical system are detected or received via one or more sensors to predict an intraocular pressure (IOP) and/or determine an IOP in real time during a surgical procedure. A notification to a surgeon or a target IOP is set and maintained as determined by Static IOP, dynamic IOP, and/or a total IOP combining both static and dynamic IOP of the anterior chamber of a patient's eye. Information collected about various components of the system are displayed on a user interface. The system uses the collected information to calculate the static IOP and/or dynamic IOP of the system, and the total IOP may be function of the static IOP and/or dynamic IOP measurements.

26 Claims, 15 Drawing Sheets

(52) U.S. Cl.
CPC .......... *A61M 1/0058* (2013.01); *A61M 1/734* (2021.05); *A61M 3/0216* (2014.02); *A61M 3/0283* (2013.01); *A61M 1/804* (2021.05); *A61M 2205/3334* (2013.01); *A61M 2205/3344* (2013.01); *A61M 2205/50* (2013.01); *A61M 2205/502* (2013.01); *A61M 2205/52* (2013.01); *A61M 2210/0612* (2013.01)

(56) References Cited

U.S. PATENT DOCUMENTS

| | | |
|---|---|---|
| 3,920,014 A | 11/1975 | Banko |
| 4,274,411 A | 6/1981 | Dotson, Jr. |
| 4,653,719 A | 3/1987 | Cabrera et al. |
| 4,702,733 A | 10/1987 | Wright et al. |
| 4,818,186 A | 4/1989 | Pastrone et al. |
| 4,832,685 A | 5/1989 | Haines |
| 4,935,005 A | 6/1990 | Haines |
| 4,954,960 A | 9/1990 | Lo et al. |
| 5,032,111 A | 7/1991 | Morris et al. |
| 5,047,009 A | 9/1991 | Morris et al. |
| 5,106,367 A | 4/1992 | Ureche et al. |
| 5,167,620 A | 12/1992 | Ureche et al. |
| 5,190,042 A | 3/1993 | Hock |
| 5,242,404 A | 9/1993 | Conley et al. |
| 5,328,456 A | 7/1994 | Horiguchi et al. |
| 5,354,268 A | 10/1994 | Peterson et al. |
| 5,405,269 A | 4/1995 | Stupecky |
| 5,417,246 A | 5/1995 | Perkins et al. |
| 5,476,448 A | 12/1995 | Urich |
| 5,487,827 A | 1/1996 | Peterson et al. |
| 5,569,188 A | 10/1996 | Mackool |
| 5,591,127 A | 1/1997 | Barwick, Jr. et al. |
| 5,616,120 A | 4/1997 | Andrew et al. |
| 5,649,905 A | 7/1997 | Zanger et al. |
| 5,695,473 A | 12/1997 | Olsen |
| 5,697,898 A | 12/1997 | Devine |
| 5,700,240 A | 12/1997 | Barwick, Jr. et al. |
| 5,733,256 A | 3/1998 | Costin |
| 5,766,146 A | 6/1998 | Barwick |
| 5,865,764 A | 2/1999 | Moorhead |
| 5,885,243 A | 3/1999 | Capetan et al. |
| 5,910,110 A | 6/1999 | Bastable |
| 5,935,106 A | 8/1999 | Olsen |
| 6,050,496 A | 4/2000 | Hefler |
| 6,159,175 A | 12/2000 | Strukel et al. |
| 6,167,588 B1 | 1/2001 | Dyson |
| 6,170,383 B1 | 1/2001 | Mauritz |
| 6,179,808 B1 | 1/2001 | Boukhny et al. |
| 6,190,354 B1 | 2/2001 | Sell et al. |
| 6,423,029 B1 | 7/2002 | Elsberry |
| 6,491,661 B1 | 12/2002 | Boukhny et al. |
| 6,533,747 B1 | 3/2003 | Polaschegg et al. |
| 6,565,535 B2 | 5/2003 | Zaias et al. |
| 6,579,255 B2 | 6/2003 | Kadziauskas et al. |
| 6,599,271 B1 | 7/2003 | Easley |
| 6,648,223 B2 | 11/2003 | Boukhny et al. |
| 6,740,058 B2 * | 5/2004 | Lal ...................... A61F 9/00745 604/65 |
| 6,780,166 B2 | 8/2004 | Kanda et al. |
| 6,986,753 B2 | 1/2006 | Bui |
| 7,083,591 B2 | 8/2006 | Cionni |
| 7,297,137 B2 | 11/2007 | Gordon et al. |
| 7,785,336 B2 | 8/2010 | Staggs |
| 8,246,580 B2 | 8/2012 | Hopkins et al. |
| 8,380,126 B1 | 2/2013 | Ma et al. |
| 8,430,841 B2 | 4/2013 | Claus et al. |
| 8,523,812 B2 | 9/2013 | Boukhny et al. |
| 8,617,106 B2 | 12/2013 | Zacharias |
| 8,715,220 B2 | 5/2014 | Gerg et al. |
| 8,721,594 B2 | 5/2014 | Zacharias |
| 9,482,563 B2 * | 11/2016 | Calderin .................. G01F 1/34 |
| 9,549,851 B2 | 1/2017 | Chon et al. |
| 9,795,507 B2 | 10/2017 | Hajishah et al. |
| 9,861,522 B2 | 1/2018 | Sorensen et al. |
| 9,931,447 B2 | 4/2018 | Layser et al. |
| 10,182,940 B2 | 1/2019 | Chandrakant et al. |
| 10,278,861 B2 | 5/2019 | Bourne |
| 10,500,319 B2 | 12/2019 | Banko |
| 2001/0023331 A1 | 9/2001 | Kanda et al. |
| 2002/0019607 A1 | 2/2002 | Bui |
| 2002/0174910 A1 | 11/2002 | Willeke, Jr. et al. |
| 2003/0006729 A1 | 1/2003 | Raymond |
| 2003/0050619 A1 | 3/2003 | Mooijman et al. |
| 2003/0078487 A1 | 4/2003 | Jeffries et al. |
| 2003/0105437 A1 | 6/2003 | Neubert |
| 2004/0092921 A1 | 5/2004 | Kadziauskas et al. |
| 2004/0101445 A1 | 5/2004 | Shvets et al. |
| 2005/0080375 A1 | 4/2005 | Kadziauskas et al. |
| 2005/0096593 A1 | 5/2005 | Pope et al. |
| 2005/0118048 A1 | 6/2005 | Traxinger |
| 2005/0209560 A1 | 9/2005 | Boukhny et al. |
| 2005/0209621 A1 | 9/2005 | Gordon et al. |
| 2005/0234441 A1 | 10/2005 | Bisch et al. |
| 2005/0261628 A1 | 11/2005 | Boukhny et al. |
| 2005/0261715 A1 | 11/2005 | Boukhny et al. |
| 2005/0267504 A1 | 12/2005 | Boukhny et al. |
| 2006/0224107 A1 | 10/2006 | Claus et al. |
| 2006/0224143 A1 | 10/2006 | Claus et al. |
| 2006/0224163 A1 | 10/2006 | Sutton |
| 2006/0281986 A1 | 12/2006 | Orilla et al. |
| 2007/0227265 A1 | 10/2007 | Sugi et al. |
| 2008/0015406 A1 | 1/2008 | Dlugos et al. |
| 2008/0033349 A1 | 2/2008 | Suzuki |
| 2008/0112828 A1 | 5/2008 | Muri et al. |
| 2008/0319374 A1 | 12/2008 | Zacharias |
| 2009/0158855 A1 | 6/2009 | Holden |
| 2009/0163863 A1 | 6/2009 | Lutwyche |
| 2010/0145302 A1 | 6/2010 | Cull et al. |
| 2010/0280435 A1 | 11/2010 | Raney et al. |
| 2011/0152728 A1 | 6/2011 | Teodorescu |
| 2011/0284777 A1 | 11/2011 | Pitchford et al. |
| 2011/0295191 A1 | 12/2011 | Injev |
| 2011/0313343 A1 | 12/2011 | Milutinovic et al. |
| 2012/0041362 A1 | 2/2012 | Gerg et al. |
| 2013/0062543 A1 | 3/2013 | Shiao et al. |
| 2013/0131578 A1 | 5/2013 | Stalmans et al. |
| 2013/0150782 A1 | 6/2013 | Sorensen et al. |
| 2013/0246079 A1 | 9/2013 | Hoffman et al. |
| 2014/0107459 A1 | 4/2014 | Lind et al. |
| 2014/0114236 A1 | 4/2014 | Gordon et al. |
| 2014/0114237 A1 | 4/2014 | Gordon et al. |
| 2014/0163455 A1 * | 6/2014 | Wilson ................ A61M 3/0258 604/22 |
| 2014/0171869 A1 | 6/2014 | Zhang |
| 2014/0206940 A1 | 7/2014 | Hufford |
| 2014/0257172 A1 | 9/2014 | Yalamanchili et al. |
| 2014/0282018 A1 | 9/2014 | Amble et al. |
| 2014/0323953 A1 * | 10/2014 | Sorensen .............. A61M 1/774 604/35 |
| 2014/0364799 A1 * | 12/2014 | Beauvais ................ A61M 1/86 604/28 |
| 2015/0157501 A1 | 6/2015 | Bourne et al. |
| 2015/0359666 A1 | 12/2015 | Zacharias |
| 2016/0128869 A1 | 5/2016 | Zacharias |
| 2016/0175578 A1 | 6/2016 | Roholt |
| 2016/0220751 A1 | 8/2016 | Mallough et al. |
| 2016/0346123 A1 | 12/2016 | Koplin |
| 2017/0022488 A1 | 1/2017 | Bermudez et al. |
| 2017/0224888 A1 | 8/2017 | Hickey et al. |
| 2017/0246419 A1 * | 8/2017 | Callaghan ........... A61M 16/203 |
| 2017/0312431 A1 | 11/2017 | Johnson et al. |
| 2017/0367885 A1 | 12/2017 | Bourne |
| 2017/0367887 A1 | 12/2017 | Muri et al. |
| 2018/0028359 A1 | 2/2018 | Gordon et al. |
| 2018/0049920 A1 | 2/2018 | Charles |
| 2018/0078415 A1 | 3/2018 | Citterio et al. |
| 2018/0279876 A1 | 10/2018 | Paschalis |
| 2018/0296738 A1 | 10/2018 | King et al. |
| 2019/0099526 A1 | 4/2019 | Hajishah et al. |
| 2019/0133822 A1 | 5/2019 | Banko |
| 2019/0143008 A1 | 5/2019 | Brundage et al. |
| 2019/0176557 A1 | 6/2019 | Marking et al. |
| 2019/0262175 A1 | 8/2019 | Kerkhoff et al. |

(56) References Cited

U.S. PATENT DOCUMENTS

| | | |
|---|---|---|
| 2019/0282401 A1 | 9/2019 | Sorensen et al. |
| 2019/0365567 A1 | 12/2019 | Balkenbush et al. |
| 2020/0030147 A1 | 1/2020 | Koplin |
| 2020/0107958 A1 | 4/2020 | Wong et al. |
| 2020/0337900 A1 | 10/2020 | Nazarifar et al. |

FOREIGN PATENT DOCUMENTS

| | | |
|---|---|---|
| EP | 1382291 A2 | 1/2004 |
| EP | 1471342 A2 | 10/2004 |
| EP | 1471342 B1 | 8/2009 |
| EP | 2379126 A2 | 10/2011 |
| EP | 2320842 B1 | 6/2012 |
| EP | 2164435 B1 | 8/2012 |
| JP | 62500640 T | 3/1987 |
| JP | 2001161740 A2 | 6/2001 |
| WO | 8906522 A2 | 7/1989 |
| WO | 9945868 A1 | 9/1999 |
| WO | 0194893 A1 | 12/2001 |
| WO | 03047653 A1 | 6/2003 |
| WO | 04108189 A2 | 12/2004 |
| WO | 04110524 A2 | 12/2004 |
| WO | 2004108189 A2 | 12/2004 |
| WO | 05037156 A1 | 4/2005 |
| WO | 2007143797 A1 | 12/2007 |
| WO | 2008030872 A1 | 3/2008 |
| WO | 2008157674 A1 | 12/2008 |
| WO | 2009076717 A1 | 6/2009 |
| WO | 2011045033 A1 | 4/2011 |
| WO | 2011105909 A1 | 9/2011 |
| WO | 2016122790 A1 | 8/2016 |
| WO | 2016150754 A1 | 9/2016 |
| WO | 2016191665 A1 | 12/2016 |
| WO | 2019068151 A1 | 4/2019 |
| WO | 2019115584 A1 | 6/2019 |

OTHER PUBLICATIONS

International Search Report and Written Opinion for Application No. PCT/IB2018/057574, dated Dec. 14, 2018, 16 pages.
International Search Report and Written Opinion for Application No. PCT/US2017/054602, dated Jan. 2, 2018, 10 pages.
International Search Report and Written Opinion for Application No. PCT/IB2018/057689, dated Jan. 24, 2019, 16 pages.
Cionni R.J., "Evaluating Two Key Safety Advances In the Centurion Vision System", ALCON, Cataract and Refractive Surgery Today, Aug. 2019, 4 pages.
Gopesh T., et al., "Rapid and Accurate Pressure Sensing Device for Direct Measurement of Intraocular Pressure", Translational Vision Science and Technology (TVST), Feb. 2020, vol. 9 (3), Article 28, pp. 1-9.
International Search Report and Written Opinion for Application No. PCT/IB2018/057699, dated Jan. 30, 2019, 15 pages.
Partial International Search Report for Application No. PCT/IB2018/057580, dated Jan. 23, 2019, 15 pages.
International Search Report for Application No. PCT/IB2020/059372, dated Dec. 22, 2020, 8 pages.
Miller K.M., et al., Millennialeye, Sep./Oct. 2019, Supplement to Cataract & Refractive Surgery Today, 16 pages.

* cited by examiner

70 ⤴

```
┌─────────────────────────────────────────────────────────┐
│        │                                                 │
│        │   IOP CALCULATION                               │
│────────┘                                                 │
│                                                         │
│   BOTTLE HEIGHT ▼ [    ]      TIP SIZE ▼ [    ]         │
│   SLEEVE SIZE ▼ [    ]        PRESSURE SUPPLY ▼ [    ]  │
│   IRRIGATION TUBE LENGTH ▼ [ ]  ASPIRATION TUBE LENGTH ▼ [ ] │
│   IRRIGATION TUBE COMPLIANCE ▼ [ ] ASPIRATION TUBE COMPLIANCE ▼ [ ] │
│   ASPIRATION RATE ▼ [    ]    VACUUM RATE ▼ [    ]      │
│                                                         │
│              [ CALCULATE ]                              │
│                                                         │
│   STATIC IOP:              DYNAMIC IOP:                 │
│                                                         │
│    16.3  mm Hg              14.1 - 18.6  mm Hg          │
│                                                         │
└─────────────────────────────────────────────────────────┘
```
66

FIG. 3

IRRIGATION PATH PRESSURE

BOTTLE HEIGHT ....
SLEEVE SIZE ....
TUBING COMPLIANCE ....
TUBING LENGTH ....

[CALCULATE]

IRRIGATION PATH PRESSURE ....

FIG. 4A

ASPIRATION PATH VACUUM PRESSURE

TIP SIZE / TYPE ....
ASPIRATION RATE ....
VACUUM RATE ....
TUBING COMPLIANCE ....
TUBING LENGTH ....
PUMP RATE ....

[CALCULATE]

ASPIRATION PATH PRESSURE ....

┌─────────────────────────────────────────┐
│     │                                   │
│     │    DYNAMIC IOP CALCULATION        │
│─────┴───────────────────────────────────│
│                                         │
│                                         │
│    IRRIGATION PATH PRESSURE ....  ____  │
│                                         │
│    ASPIRATION PATH VACUUM PRESSURE .... ____ │
│                                         │
│              ┌───────────┐              │
│              │ CALCULATE │              │
│              └───────────┘              │
│                                         │
│    DYNAMIC IOP .... ____ - ____ mm Hg   │
│                                         │
└─────────────────────────────────────────┘
                                         66

| TOTAL IOP CALCULATION |
|---|

STATIC IOP .... _____ mm Hg

DYNAMIC IOP .... _____ - _____ mm Hg

WOUND LEAKAGE .... [▼_____]

[CALCULATE]

TOTAL IOP .... _____ mm Hg

SYSTEMS AND METHODS FOR MEASURING FLUID FLOW IN A VENTURI BASED SYSTEM

CROSS REFERENCES TO RELATED APPLICATIONS

This application claims the benefit under 35 U.S.C. § 119(e) of U.S. Provisional Patent Application No. 62/568,174, filed Oct. 4, 2017, which is incorporated herein by reference in its entirety.

BACKGROUND

Field of Invention

The present disclosure relates generally to medical apparatuses and methods that provide pressurized infusion of liquids for ophthalmic surgery, and more particularly, to medical apparatuses and methods that require determinable, stable or controlled intraoperative intraocular pressure (IOP) within the anterior chamber of the eye.

Description of Related Art

During ophthalmic surgery, an ophthalmic surgical apparatus is used to perform surgical procedures in a patient's eye. An ophthalmic surgical apparatus typically includes a handheld medical implement or tool, such as a handpiece with a tip and/or sleeve, and operating controls for regulating settings or functions of the apparatus and tool. Operation of the tool requires control of various operating settings or functions based on the type of tool used. Such apparatuses typically include a control module, power supply, an irrigation source, one or more aspiration pumps, as well as associated electronic hardware and software for operating a multifunction handheld surgical tool. The handpiece may include a needle or tip which is ultrasonically driven once placed with the incision to, for example, emulsify the lens of the eye. In various surgical procedures, these components work together in order to, for example, emulsify crystalline lens, irrigate the eye with a saline solution, and aspirate the emulsified lens from the eye.

An exemplary type of ophthalmic surgery is phacoemulsification. Phacoemulsification includes making a corneal and/or scleral incision and the insertion of a phacoemulsification handpiece that includes a needle or tip that is ultrasonically driven to emulsify, or liquefy, the lens. A phacoemulsification system typically includes a handpiece coupled to an irrigation source and an aspiration pump. The handpiece includes a distal tip that emits ultrasonic energy to emulsify a crystalline lens within the patient's eye. The handpiece includes one or more irrigation ports proximal to the distal tip and coupled to the irrigation source via an irrigation input line. The handpiece further includes an aspiration port at the distal tip that is coupled to the aspiration pump via an aspiration output line. Concomitantly with the emulsification, fluid from the irrigation source (which may be a bottle or bag of saline solution that is elevated above the patient's eye, to establish positive pressure by gravity, and/or with external pressure source) is irrigated into the eye via the irrigation line and the irrigation port(s). This fluid is directed to the crystalline lens in the patient's eye in order to maintain the anterior chamber and capsular bag and replenish the fluid aspirated away with the emulsified crystalline lens material. The irrigation fluid in the patient's eye and the crystalline lens material is aspirated or removed from the eye by the aspiration pump and line via the aspiration port. In some instances, the aspiration pump may be in the form of, for example, a peristaltic or positive displacement pump. Other forms of aspiration pumps are well known in the art, such as vacuum pumps. In addition, more than one pump or more than one type of pump may be used. Additionally, some procedures may include irrigating the eye and aspirating the irrigation fluid without concomitant destruction, alteration or removal of the lens.

Intraocular pressure (IOP) is the fluid pressure inside the anterior chamber of the eye. In a normal eye, intraocular pressure may vary depending on the time of day, activities of the patient, fluid intake, medications, etc. Intraoperative intraocular pressure may be measured as static (a specific value) or dynamic (a range of values). As can be appreciated, the static IOP and dynamic IOP of a patient's eye can fluctuate greatly during an ophthalmic surgery procedure. It is well known that the IOP in an anterior chamber of the eye is required to be controlled and maintained during such surgical procedures in order to avoid damage to the patient's eye. For the correct function of the eye and its structure (e.g. shape) and to preserve sharp and undamaged vision, it is very important to maintain the intraoperative IOP.

Different medically recognized techniques have been utilized for ophthalmic surgery, such as phacoemulsification, in order to maintain and control the intraoperative IOP of a patient's eye. In various examples, phacoemulsification may involve combining irrigation, aspiration and emulsification within a single handpiece. The handpiece that is typically controlled electrically in order to, for example, control the flow of fluid through the handpiece and tip. As may be appreciated, during a surgical procedure, the flow of fluid to and from a patient's eye (through a fluid infusion/irrigation system or aspiration/extraction system, for example), the fluid pressure flowing through the handpiece, and the power control over the handpiece, are all critical to the procedure performed. Precise control over aspiration and irrigation to the anterior chamber is desired in order maintain a desired or optimal intraoperative IOP within the anterior chamber of the eye. Similarly, it may be necessary to maintain a stable volume of liquid in the anterior chamber of the eye, which may be accomplished by irrigating fluid into the eye at the same rate as aspirating fluid and lens material from the eye. Accordingly, the ability to predict or determine the static IOP and dynamic IOP of a patient's eye during a surgical operation would be beneficial to a surgeon or operator of such a surgical apparatus.

In prior ophthalmic surgical devices, the control and settings of the system may be electronically controlled or modified by use of a computer system, control module and/or a user/surgeon. For instance, the control module may also provide feedback information to a user or surgeon regarding the function and operation of the system, or may also receive input from a user or surgeon in order to adjust surgical settings. A surgeon or user may interface with a display system of the control module during use of the device.

Additionally, a surgeon or user may control or adjust certain aspects of the intraoperative IOP by adjusting various settings or functions of the system. For instance, the irrigation source may be in the form of a suspended or lifted saline bottle or bag, and the surgeon is typically able to adjust the height of the bottle or bag to create a specific head height pressure of the fluid flowing from the bottle or bag. In typical systems, the head height pressure, which is a function of the column height, is the static IOP of the fluid flowing through the patient's eye. Accordingly, the surgeon may be able to indirectly set the static IOP by changing the bottle height to a desired level. However, dynamic IOP is a function of surgical parameters and the surgical environment during surgery. Currently, ophthalmic systems do not provide any means for measuring or predicting dynamic IOP.

Even further, prior phacoemulsification systems do not provide a process to manage IOP during post occlusion surge thereby affecting anterior chamber stability. Further, prior phacoemulsification systems do not provide any indication of occlusion or post occlusion surge events.

Current phacoemulsification systems, both based on peristaltic and Venturi systems may not provide suitable methods of managing IOP during post occlusion surge, often resulting in uncontrolled changes to the stability of the anterior chamber. More specifically, current Venturi based systems, including those using a gravity based infusion system, may not provide any indication(s) relative to post occlusion surge events. For example, if a phacoemulsification needle tip is occluded with cataract material, a high vacuum state may be created within the outflow tubing. This high vacuum level may at least partially collapse the walls of the elastic tubing, and, once the occlusion breaks, the walls of the tubing may rebound back into shape, rapidly sucking fluid from the eye and creating a surge. Because the volume of the anterior and posterior chambers are so small, a slight collapse in the length of the long outflow tubing may create a significant surge and increase the risk for collapse of the eye and aspiration of the posterior capsule during surgery. Thus, the management and quantification of IOP and occlusion, and post occlusion surge detection, may provide improved fluidics control during phacoemulsification surgery and may lead to better surgical outcomes by improving anterior chamber stability and more reliable surgical systems.

Based on the foregoing, it would be advantageous to provide a means for determining both the static IOP and dynamic IOP of a patient's eye throughout a surgical operation. Further, it would be advantageous to provide a means for determining a total IOP for the patient's eye from the static IOP, dynamic IOP, and/or other variables of the surgical operation. Such a design would afford a surgeon the ability to perform desired phacoemulsification, diathermy, or vitrectomy functions with better understanding of the surgical environment and process during the surgical procedure.

SUMMARY

The present invention provides a system for varying pressure rates during phacoemulsification surgery. The system comprises a surgical console having at least one system bus communicatively connected to at least one computing processor capable of accessing at least one computing memory associated with the at least one computing processor, a phacoemulsification surgical handpiece having at a distal end at least one surgical tool and having near a proximal end of a first pressure sensor communicatively connected to an aspiration line, and a second pressure sensor communicatively connected to the aspiration line and proximate to a vacuum source associated with the surgical console, wherein the pressure of the aspiration line is regulated in accordance with a comparison between an estimated aspiration flow calculated from the pressure measured by the first and second sensors and a predetermined aspiration pressure.

The system of the present invention may comprise a surgical console having at least one system bus communicatively connected to at least one computing processor capable of accessing at least one computing memory associated with the at least one computing processor, a phacoemulsification surgical handpiece having at a distal end at least one surgical tool and having near a proximal end a detachable receiver for receiving an aspiration line and an irrigation line from the surgical console, a first pressure sensor communicatively connected to the aspiration line and located proximate to the detachable receiver, and a second pressure sensor communicatively connected to the aspiration line and proximate to a vacuum source associated with the surgical console, wherein the pressure of the irrigation line is regulated in accordance with an estimated aspiration flow calculated from the pressure measured by the first and second sensors.

The system of the present invention may comprise a surgical console having at least one system bus communicatively connected to at least one computing processor capable of accessing at least one computing memory associated with the at least one computing processor, a phacoemulsification surgical handpiece having at a distal end at least one surgical tool and having near a proximal end of a mass air flow sensor communicatively connected to an aspiration line, and wherein the pressure of the aspiration line is regulated in accordance with a comparison between an estimated aspiration flow calculated from the pressure measured by the mass air flow sensor and a predetermined aspiration pressure.

BRIEF DESCRIPTION OF THE DRAWINGS

The organization and manner of the structure and function of the disclosure, together with the further objects and advantages thereof, may be understood by reference to the following description taken in connection with the accompanying drawings, and in which:

FIG. 3 illustrates an embodiment of a graphical user interface of the system of FIG. 1 or 2, illustrating means for inserting various variables into the control module to permit the control module to determine static and/or dynamic IOP calculation(s);

FIG. 4A illustrates an embodiment of a graphical user interface of the system of FIG. 1 or 2, further illustrating means for calculating irrigation path pressure;

FIG. 4B illustrates an embodiment of a graphical user interface of the system of FIG. 1 or 2, further illustrating means for calculating aspiration path vacuum or pressure;

FIG. 5 illustrates an embodiment of a graphical user interface of the system of FIG. 1 or 2, further illustrating a calculation means for determining a dynamic range of IOP during a surgical operation;

FIG. 6 illustrates an embodiment of a graphic user interface of the system of FIG. 1 or 2, further illustrating means for calculating the total IOP based on the static and dynamic IOP variables;

DETAILED DESCRIPTION

Figure 1:
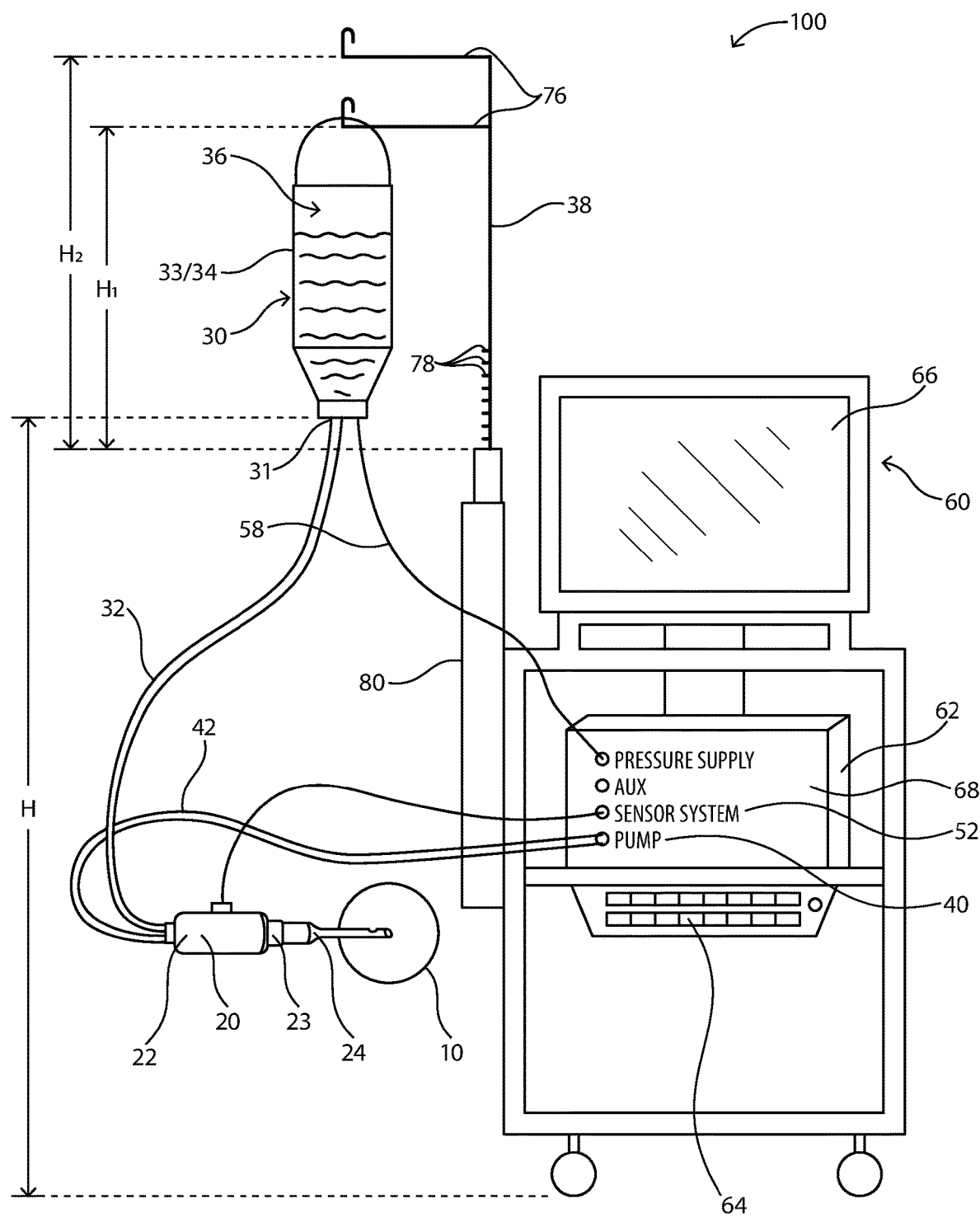
FIG. 1 illustrates a diagram of an exemplary phacoemulsification/diathermy/vitrectomy system in accordance with the present disclosure, the system including a control module to control various features of the system.

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

A system and method for receiving and/or detecting certain variables of a surgical system and utilizing those variables to predict an intraoperative intraocular pressure (IOP) and/or determine an IOP in real time during a surgical procedure to either provide a notification to a surgeon or allow a target IOP of the anterior chamber of a patient's eye to be set and maintained may be determined by Static IOP, dynamic IOP, and/or a total IOP combining both static and dynamic IOP of the anterior chamber of a patient's eye, which can be applied to any type of system, are disclosed herein. For example, the IOP may be segmented into static and dynamic during a phacoemulsification procedure, static IOP being primarily impacted by the fluid inflow with small amount of outflow and dynamic IOP being primarily impacted by fluid outflow. In illustrative embodiments, the system and method include means for calculating the static IOP, dynamic IOP, and/or total IOP through information provided by a user (e.g. a surgeon) of the system or information collected by a control module of the system. In illustrative embodiments, the system and method include a graphical user interface or other user interface that permits a user to insert information about various components of the system. In other illustrative embodiments, the system can determine various parameters of the system through internal sub-systems (e.g. sensors) to collect information about various components of the system and display such information on the user interface. The system may use such information to calculate the static IOP and/or dynamic IOP of the system, and the total IOP may be function of the static IOP and/or dynamic IOP measurements. In addition, as will be discussed additional parameters or factors may also be considered in determining a total IOP.

As discussed herein, a stable intraoperative IOP may be of critical importance in order to maintain a stable anterior chamber pressure during phacoemulsification. A stable intraoperative IOP may be a function of fluid inflow and outflow such that the volume, and in turn the pressure of anterior chamber, remains stable when a chamber is at or near equilibrium.

Further, parameters directed towards IOP, occlusion, and post occlusion surge detection would provide a better fluidics control and in turn lead to improved anterior chamber stability, thereby providing comfort to a patient, an operating surgeon and ensure safety while using phacoemulsification systems.

Embodiments of a subsystem and method will be discussed herein with a particular emphasis on a medical or hospital environment where a surgeon or health care practitioner performs. For example, an embodiment is a phacoemulsification surgical system that comprises an integrated high-speed control module for a phacoemulsification or vitrectomy handpiece that is configured to be inserted into a patient's eye during the phacoemulsification procedure. The system may further comprise one or more sensor(s) to detect variables about the function and operation of the system, such as the rate of fluid flow before and after the fluid flows through the handpiece, and a processor that can collect such variables and/or receive additional variables as inputs from a user, in order to determine the static IOP and dynamic IOP of the anterior chamber of the patient's eye during surgery. The system may further comprise a processor that may control, adjust or set various characteristics of the system to control a phacoemulsification or a high-speed pneumatic or electronic vitrectomy handpiece based on the static IOP and/or dynamic IOP measurements determined.

Figure 2:
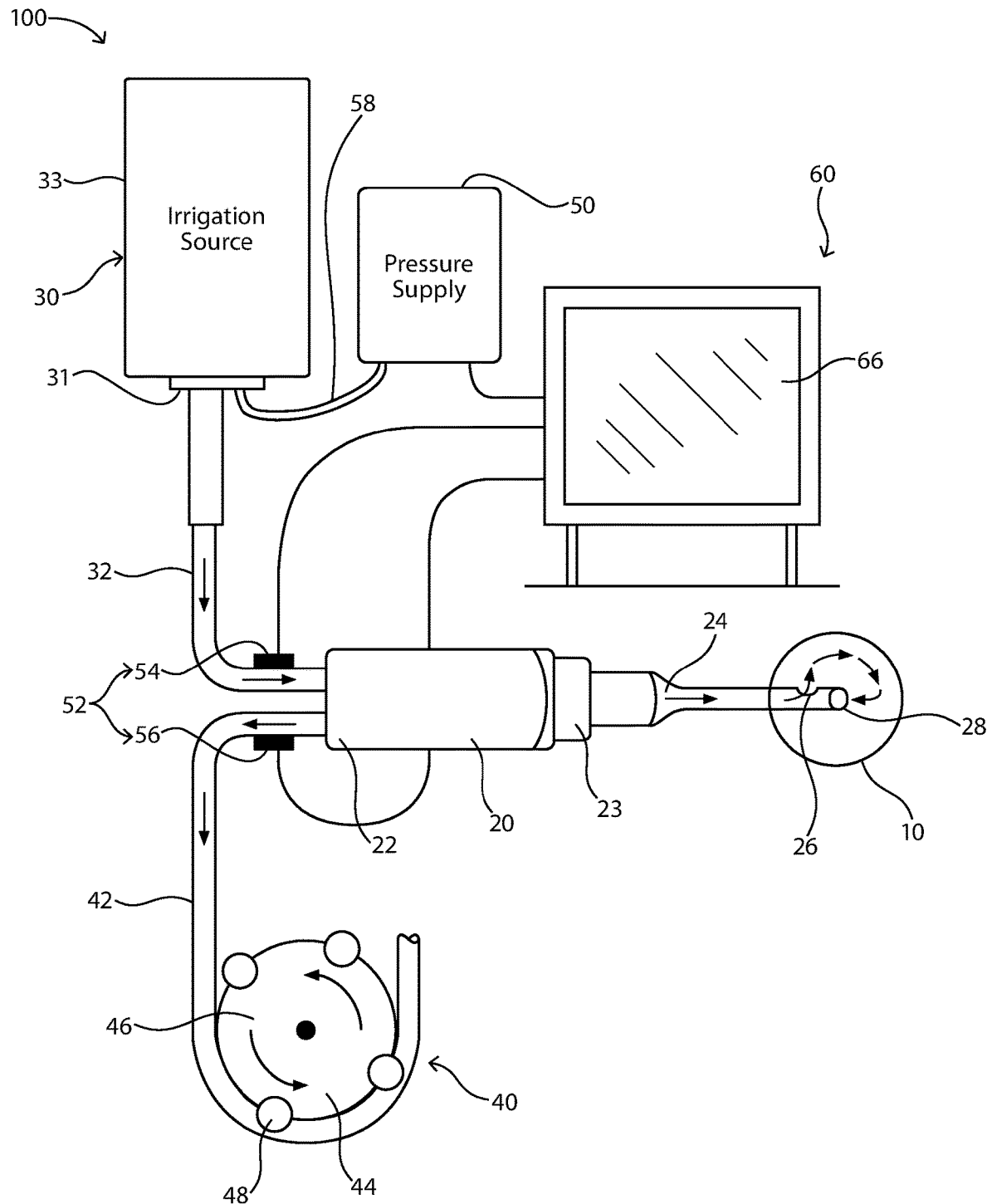
FIG. 2 illustrates an alternative phacoemulsification/diathermy/vitrectomy system and illustrated connected to various components of the system in order to determine characteristics or features of the components.

FIGS. 1 and 2 illustrate an exemplary phacoemulsification/diathermy/vitrectomy system 100. As illustrated, the system 100 includes, for example, a handpiece or wand 20, an irrigation source 30, an aspiration source 40, an optional pressure supply 50, and a control module 60. In illustrative embodiments, fluid is controllably directed through the system 100 in order to irrigate a patient's eye, illustrated representatively at 10, during an ocular surgical procedure. Various embodiments of the handpiece 20, irrigation source 30, aspiration source 40, optional pressure supply 50 and control module 60 are well known in the art and are embodied in this disclosure.

As illustrated in FIGS. 1 and 2, the irrigation source 30 is configured to supply a predetermined amount of fluid to the handpiece 20 for use during a surgical operation. Such fluid is supplied in order to, for example, stabilize or maintain a certain IOP in the anterior chamber of the eye during surgery, as well as provide means for fluidly transporting any particles (e.g. lens particulates that are created during emulsification) out of the eye. Various aspects (e.g. the flow rate, pressure) of fluid flow into and out of the anterior chamber of the eye will typically affect the operations of the surgical procedure and in particular the IOP measurements of the anterior chamber of the eye during the surgical procedure.

In illustrative embodiments, fluid may flow from the irrigation source 30 to the handpiece 20 via an irrigation line 32. The irrigation source 30 may be any type of irrigation source 30 that can create and control a constant fluid flow. In illustrative embodiments, the irrigation source is elevated to a predetermined height via an extension arm 38. In illustrative embodiments, the irrigation source 30 may be configured to be an elevated drip bag 33/34 that supplies a steady state of fluid 36 to the irrigation line 32. The pressure supply 50 may be coupled to the irrigation source 30 in order to maintain a constant pressure in the irrigation source 30 as fluid exits the irrigation source 30, as is known in the industry. Other embodiments of a uniform irrigation source are well known in the art.

During the surgical procedure, it is typically necessary to remove or aspirate fluid and other material from the eye. Accordingly, fluid may be aspirated from the patient's eye, illustrated representatively at 10, via the handpiece 20 to flow through an aspiration line 42 to the aspiration source 40. The aspiration source 40 may be any type of aspiration source 40 that aspirates fluid and material from the eye. In illustrative embodiments, the aspiration source 40 may be configured to be a flow-based pump 44 (such as a peristaltic pump) or a vacuum-based pump (such as a Venturi pump) that are well known in the art. The aspiration source 40 may create a vacuum system to pump fluid and/or material out of the eye via the aspiration line 42. Other embodiments of an aspiration source are well known in the art.

The irrigation port 26 is fluidly coupled to the irrigation line 32 to receive fluid flow from the irrigation source 30, and the aspiration port 28 is fluidly coupled to the aspiration line 42 to receive fluid and/or material flow from the eye. The handpiece 20 and the tip 24 may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well known in the art. Concomitantly with the emulsification, fluid from the irrigation source 30 is irrigated into the eye via the irrigation line 32 and the irrigation port 26. During and after such emulsification, the irrigation fluid and emulsified crystalline lens material are aspirated from the eye by the aspiration source 40 via the aspiration port 28 and the aspiration line 42. Other medical techniques for removing a crystalline lens also typically include irrigating the eye and aspirating lens parts and other liquids. Additionally, other procedures may include irrigating the eye and aspirating the irrigating fluid within concomitant destruction, alternation or removal of the lens.

The aspiration source 40 is configured to aspirate or remove fluid and other materials from the eye in a steady, uniform flow rate. Various means for steady, uniform aspiration are well known in the art. In illustrative embodiments, the aspiration source 40 may be a Venturi pump, a peristaltic pump, or a combined Venturi and peristaltic pump. In illustrative embodiments, and as shown in FIG. 2, a peristaltic pump 44 may be configured to include a rotating pump head 46 having rollers 48. The aspiration line 42 is configured to engage with the rotating pump head 46 as it rotates about an axis. As the pump head 46 rotates the rollers 48 press against the aspiration line 42 causing fluid to flow within the aspiration line 42 in a direction of the movement for the rollers 48. Accordingly, the pump 44 directly controls the volume or rate of fluid flow, and the rate of fluid flow can be easily adjusted by adjusting the rotational speed of the pump head 46. Other means of uniformly controlling fluid flow in an aspiration source 40 are well known in the art. When the aspiration source 40 includes a combined Venturi and peristaltic pump, the aspiration source 40 may be controlled to automatically switch between the two types of pumps or user controlled to switch between the two types of pumps.

In illustrative embodiments, the control module 60 is configured to monitor and control various components of the system 100. For instance, the control module 60 may monitor, control, and provide power to the pressure supply 50, the aspiration source 40, and/or the handpiece 20. The control module 60 may be in a variety of forms as known in the art. In illustrative embodiments, the control module 60 may include a microprocessor computer 62, a keyboard 64, and a display or screen 66, as illustrated in FIGS. 1, 2A, 3, 4 and 5. The microprocessor computer 62 may be operably connected to and control the various other elements of the system, while the keyboard 64 and display 66 permit a user to interact with and control the system components as well. In an embodiment a virtual keyboard on display 66 may be used instead of keyboard 64. In illustrative embodiments, the control module 60 may also include a pulsed ultrasonic power source (not shown) that can be controlled by the computer 62 in accordance with known methods or algorithms in the art. A system bus 68 may be further provided to enable the various elements to be operable in communication with each other.

The screen 66 may display various measurements, criteria or settings of the system 100—such as the type of procedure, the phase of the procedure and duration of the phase, various parameters such as vacuum, flow rate, power, and values that may be input by the user, such as bottle height or infusion pressure, sleeve size, tube length (irrigation and aspiration), tip size, vacuum rate, etc., as illustrated in FIGS. 3-5. The screen 66 may be in the form of a graphical user interface (GUI) 70 associated with the control module 60 and utilizing a touchscreen interface, for example. The GUI 70 may allow a user to monitor the characteristics of the system 100 or select settings or criteria for various components of the system. For instance, the GUI 70 may permit a user to select or alter the maximum pressure being supplied by the pressure supply 50 to the irrigation source 30 via line 58. The user may further control the operation of the phase of the procedure, the units of measurement used by the system 100, or the height of the irrigation source 30, as discussed below. The GUI 70 may further allow for the calibration and priming of the pressure in the irrigation source 30.

In illustrative embodiments, the system 100 may include a sensor system 52 configured in a variety of ways or located in various locations. For example, the sensor system 52 may include at least a first sensor or strain gauge 54 located along the irrigation line 32 and a second sensor or strain gauge 56 located along the aspiration line 42, as illustrated in FIG. 2. Other locations for the sensors 54 and 56 are envisioned anywhere in the system 100, e.g. on the handpiece 20, and may be configured to determine a variety of variables that may be used to determine intraoperative IOP measurements in the eye, as discussed below. This information may be relayed from the sensor system 52 to the control module 60 to be used in the determination of IOP measurements. The sensor system 52 may also include sensors to detect other aspects of the components used in the system, e.g. type of pump used, type of sleeve used, gauge of needle tip (size), etc.

In order to determine the IOP of a patient's eye during surgery, the system 100 may be configured to determine and/or receive a variety of variables about the system 100 that may be used in a predictive algorithm to determine the IOP range before the surgery begins or provide the IOP during surgery based on the entered parameters and/or sensed parameters. The algorithm may be performed on the control module 60 and takes into account one or more of the parameters, such as bottle height, tip size, sleeve size, aspiration rate, vacuum rate, length and compliance metrics of various tubing used in the system, and/or pump rate, as will be described below. Other parameters for consideration in the algorithm are envisioned within the scope of this disclosure. Specifically, the following algorithms alone or in combination in addition to other parameters discussed below may be used to determine IOP measurements:

Static IOP=function {bottle height, wound leakage, sleeve size, length of irrigation tubing, and/or inside diameter of irrigation tubing}

Dynamic IOP=function {tip size, aspiration rate, vacuum rate, aspiration tubing length, inside diameter of aspiration tubing, tubing compliance,}

Other Parameters to Consider: Patient Eye Level

The variables of these algorithms will now be discussed.

One factor for consideration in the determination of IOP measurement is the bottle height of the irrigation source 30. As illustrated in FIG. 1, the irrigation source 30, specifically the exit port 31 of the irrigation source, is typically elevated to a predetermined height H. This predetermined elevation may be accomplished by any known means. For example, the irrigation source 30 may be connected to one or more fixed supports 76 on the extension arm 38, the fixed supports spaced at varying heights H1 and H2 along the extension arm 38 to permit the irrigation source 30 to hang down via the force of gravity and place the exit port 31 of the irrigation source 30 at predetermined height H. Alternatively, the extension arm 38 may be retractable (or movable) relative to a fixed receiver 80, the extension arm 38 including biased retaining members 78 that can engage with an aperture (not shown) of the fixed receiver 80 to maintain the extension arm 38 in a relative position with respect to the fixed receiver 80. In such an embodiment, the height H of the exit port 31 of the irrigation source 30 (with respect to the ground) may be maintained in the predetermined position based on the specific retaining member 78 engaging with the aperture of the fixed receiver 80, as is known in the art. Other means of height adjustment are known in the art.

The bottle height may be inputted manually into the control module 60 of the system by a user via a graphical user interface 70. Alternatively, the bottle height may be determined by the control module 60 automatically and displayed on the graphical user interface 70. For example, a sensor system (not shown) may be connected to the extension arm 38 or the fixed receiver 80 to determine the height H of the exit port 31.

Another factor for consideration in the determination of IOP measurement is the size of a sleeve 90 around needle 24. The size of a sleeve or dimension of a sleeve can be a factor in the amount of fluid that flows from irrigation source 30 into the eye.

The size of the sleeve 90 may be inputted manually into the control module 60 of the system by a user via a graphical user interface 70. Alternatively, the size of the sleeve 90 may be determined automatically by the control module 60 and displayed on the graphical user interface 70. For example, a sensor system (not shown) may be connected to the handpiece 20 and/or near the sleeve 90. During a calibration or prime and tune cycle of the system 100, the system may be able to determine the size of the sleeve 90 by comparing information received from the sensor, e.g. on the amount of fluid flow out of the sleeve based on the height of the bottle or the flow rate if a pressurized system is used. For example, the sleeve size may be based on the gauge of the needle used or selected independently of the needle selected. In an embodiment of the present invention, where a basic level of IOP is to be determined, a static IOP may be a function of fluid inflow only, where fluid inflow is governed by the column height of the bottle (bottle height) and wound leakage. As discussed herein, column height of the fluid may be governed by IV bottle height or other pressurizing source such as, for example, vented gas forced infusion (VGFI) and/or incision wound leakage. By way of example, as the height of the IV bottle changes, the static IOP would change accordingly. A surgeon may therefore set the desired static IOP before and during the surgery by adjusting the bottle height or other pressurizing source. The pressure exerted by the bottle height of the fluid is governed by following function:

Pressure (mmHg)=Column Height (cm)×10/density of the fluid (for example, the fluid may be mercury, the density of which is assumed to be 13.6 g/cm$^3$, or water, which has a density of 1 g/cm$^3$).

Assuming that the amount of wound leakage is governed by the size of incision, the static IOP=function {Bottle Height, Wound Leakage}. Using this function, the system of the present invention may determine the bottle height by measuring the IV pole height or input pressure of the pressurizing source.

In another embodiment of the present invention, additional parameters are considered in determining IOP is described. During phacoemulsification, for example, the IOP of the anterior chamber may vary as lens fragments are emulsified and aspirated from the anterior chamber of the eye. Such variability is a result of the dynamic nature of intraocular pressure during the phacoemulsification procedure. In an embodiment of the present invention, dynamic IOP may be governed by the flow or aspiration rate. During a procedure, flow and vacuum rates may change as fragments are emulsified and aspirated. This may cause changes in volume of the anterior chamber which in turn may cause the IOP to vary. Thus, the Total IOP may take into account Static IOP parameters and Dynamic IOP parameters. The Total IOP may be predicted before the surgery and also may be determined during surgery based on real time measurements. In addition, a target IOP a surgeon would like to maintain in a patient's eye may be set and the system may adjust various system components or parameters based on sensed data used to calculate periodic Total IOPs during the surgery to maintain the target IOP. Thus, based on the example described above, the Total IOP=Static IOP function {Bottle Height, Wound Leakage}+Dynamic IOP function {Flow Rate/Aspiration Rate}. Using this algorithm, the system of the present invention may determine the bottle height by measuring IV pole height or input pressure of the pressurizing source. Wound leakage may be determined by the size of the incision made during the surgery. Further, the system of the present invention may determine fluid outflow by measuring the flow rate at the aspiration line. Moreover, based on the system calculating the Total IOP at various time points before and/or during the procedure a target IOP may be maintained by adjusting one or more parameters, e.g. irrigation flow rate, bottle height, aspiration rate, etc.

In another embodiment of the present invention, a predictive IOP algorithm may be further optimized to provide a more accurate prediction of Total IOP during surgery by taking into account additional parameters, such as the tip and sleeve sizes along with the compliance and length of the associated tubing apparatus. Such an algorithm may use the above stated parameters to provide one or more IOP measurements before and/or during surgery. Thus, the Total IOP=Static IOP {fluid inflow}+Dynamic IOP {fluid outflow}; wherein fluid inflow=function {bottle height or input pressure, sleeve size, wound leakage, length of the irrigation tubing, and inside diameter of irrigation tubing} and fluid outflow=function {flow/aspiration rate, vacuum rate, tip size, compliance, length and inside diameter of aspiration tubing}.

Bottle height may be obtained by measuring the IV pole height and/or input pressure of the pressurizing source and the patient eye level is input prior to the surgery and does not change during the surgery. Generally, the sleeve size is fixed during the surgery and a user may either provide the type and size of the sleeve used or the system may infer this value by measuring the out flow from the sleeve during the prime and tune processes. Flow rate may be variable during a surgery and the system may obtain a flow rate value by measuring the flow of fluid through the aspiration line, while a maximum aspiration rate is generally preset by a user prior to starting a surgery. The vacuum rate may be variable during the surgery and the system may obtain a value for the vacuum rate by measuring the running vacuum during surgery. The length of the irrigation/aspiration (FA) tubing is generally defined as the distance from the end of the hand piece to the pack or cassette. The system may infer this value from the type of pack used. Compliance of the FA tubing may be defined for each type of pack such as, for example, a single-use pack or multi-use pack. The system may infer this value from type of pack used. Similarly, the inside diameter of the FA tubing may be defined for each type of pack, which value may be inferred from type of pack used.

Another factor for consideration in the determination of IOP measurement is tip size. In illustrative embodiments, the tip 24 of the handpiece 20 may be interchangeable with several other interchangeable tips 24 that have different features or characteristics. These tips 24 may have predetermined or uniform shapes and port sizes/locations based on the specific tip selected, so that a certain tip size is an industry standard and is known to have industry standard dimensions and features. Each of the different tip sizes may include or provide benefit in the way of different features that assist with performing the surgical operation. Such tips 24 are generally known to be of uniform sizes or types in the industry, such that certain tips 24 may be considered advantageous for certain surgical maneuvers or operations. Tips of uniform size or type may be identified by specific name or product number to be an industry standard design. Surgeons or other users of such tips may have industry knowledge of the types of tips available and their varying characteristics, and may rely on the uniformity of tip types from operation to operation.

The tip size may be inputted manually into the control module 60 of the system 100 by a user via the graphical user interface 70. Alternatively, the tip size may be determined by the control module 60 automatically and displayed on the graphical user interface 70. In this regard, applicant refers to U.S. Patent Application No. 62/293,283, incorporated by reference herein.

Other factors for consideration in the determination of IOP measurement are the characteristics of the irrigation and aspiration lines 32, 42 (e.g. tubing). As illustrated in FIGS. 1 and 2, the irrigation line 32 connects the irrigation source 30 to the handpiece 20 and delivers fluid to the handpiece 20, and the aspiration line 42 connects the handpiece 20 to the aspiration source 40 and removes fluid from the eye via the handpiece 20. These lines 32, 42 typically comprise flexible tubing that permits a wide variety of relative movement of the handpiece 20 with respect to the irrigation source 30 and aspiration source 40. The flexible tubing selected for the system may include a variety of lengths and diameters. The length of tubing between the irrigation source 30 and the handpiece 20, and the handpiece 20 and the aspiration source 40, affects the fluid flow and fluid pressure when the fluid enters/leaves the patient's eye. Similarly, the inside diameter of the tubing affects the fluid flow and fluid pressure when the fluid enters/leaves the eye. Similar to the dimensions of the irrigation line 32 and aspiration line 42, the composition of the lines may also affect the flow or pressure of fluid into and out of the patient's eye. Tubing is typically required to meet certain industry standards of compliance, and further be identified based on the compliance requirements of the tubing. The composition (e.g. type of material used to form the tubing) may have certain characteristics (such as compression strength, pliability, etc.) that affect the fluid flow and fluid pressure of fluid flowing into or leaving the patient's eye.

The characteristics of the irrigation and aspiration tubing may be inputted manually into the control module 60 of the system 100 by a user via the graphical user interface 70. Alternatively, a user may be able to select specific tubing based on predetermined requirements identified by the system 100 once a desired IOP is determined. A sensor system (not shown) may exist to determine the compliance, length and diameter of the tubing, alternatively.

Other factors for consideration in the determination of IOP measurement are the characteristics of the aspiration source 40, including the aspiration rate (e.g. rate fluid is aspirated from the eye), vacuum rate (e.g. rate of the vacuum in the aspiration source). The characteristics of the aspiration source 40 may be inputted manually into the control module 60 of the system 100 by a user via the graphical user interface 70, may be preprogrammed in the system, or may be determined by a sensor system (not shown) located along the aspiration line 42 or in the aspiration source 40.

In any of the embodiments described herein, any number of the parameters may be used or values entered by a user or considered by the algorithm when calculating a Total IOP. The more parameters used the more accurate the Total IOP is likely to be.

FIGS. 3-5 illustrate exemplary embodiments of a graphical user interface 70 that permits collection and/or display of variables that can affect the static IOP and dynamic IOP when calculating a Total IOP measurement. A variety of methods of collecting and/or displaying information may be encompassed in this disclosure. For example, FIG. 3 illustrates a single-screen IOP calculation on GUI 70, permitting a user to insert two parameters related to the algorithms to calculate a basic Total IOP measurement, as discussed above, and presenting the resulting Total IOP measurement determined from the algorithm calculation. FIG. 4 illustrates a single-screen IOP calculation on GUI 70, permitting a user to insert values for the parameters for both Static IOP and Dynamic IOP to calculate a Total IOP measurement as discussed above, and presenting the resulting Total IOP measurement determined from the algorithm calculation. FIG. 5 illustrates a single-screen IOP calculation on GUI 70, permitting the user to input values for one or more parameters for the Static IOP and/or Dynamic IOP, in addition to the option of entering the patient eye level, to calculate a Total IOP measurement discussed above, and presenting the resulting Total IOP measurement determined from the algorithm calculation. It is also envisioned that each time an IOP calculation is made during surgery it is displayed to a user. In an embodiment, should a target IOP or target range of IOPs be set by a user a visual and/or audible signal can be made to alert the user when the measured IOP falls outside a preset range of the selected or preselected target IOP or target range of IOPs. In addition, to the signal, the system may automatically adjust system parameters to bring the patient's IOP back to the target IOP or within the selected target range of IOP.

FIG. 6 illustrates means for calculating the total IOP on the GUI 70 as a function of the static IOP measurement, the dynamic measurement, and an optical variable related to wound leakage that may be inputted by a user of the system.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.), irrigation source height adjustment, linear control of settings, proportional control of settings, panel control of settings, and type (or "shape") of response.

In illustrative embodiments, the interface provides feedback to the user should the predetermined or automatic settings, variables, or criteria need adjustment to ensure all the desired settings of the system. The interface can then permit the user to change or modify those settings accordingly.

Other mechanisms for setting and/or programming a particular setting may be employed with the present invention, including, but not limited to, clicking on an icon on a display screen using a mouse or touch screen, depressing a button/switch on a foot pedal, voice activated commands and/or combinations thereof.

In an embodiment of the present invention, irrigation pressure and/or aspiration vacuum at, or in near proximity to, the phacoemulsification hand piece may be measured in real time. Existing phacoemulsification handpieces do not provide a method to measure pressure on or within the irrigation and/or aspiration lines. Measuring pressure on the irrigation and/or aspiration lines in close proximity to the phacoemulsification handpiece may allow for more accurate and precise estimation of the pressure at the surgical site, such as in, for example, a patient's anterior chamber of the eye. More accurate pressure and vacuum measurements, for example, may be utilized to develop algorithms to provide more robust fluidics control during phacoemulsification surgery which may lead to the improvement of anterior chamber stability. This, in turn, may provide additional comfort to the patient, control over the surgical parameters to the operating surgeon, and ensure safer operation of peristaltic and/or Venturi based pumps during phacoemulsification surgery.

In an embodiment of the present invention, an in-line irrigation pressure sensor and aspiration vacuum sensor may be located on or proximate to the hand piece may provide real-time irrigation and aspiration vacuum data. The proximity of pressure sensors to the surgical site during phacoemulsification surgery may allow for increased monitoring of, for example, the anterior chamber environment. Data collected from one or more of the sensors may allow for the development of an algorithm which may be used to monitor intraocular pressure, and predict occlusion and post occlusion surge events during surgery more accurately and in a more timely manner than is currently available. Using the developed algorithm, discussed herein below, the system may adjust the irrigation and/or aspiration rates in order to improve, for example, anterior chamber stability. Similarly, when the aspiration slows down, fluid circulation may recede and the heat generated from the handpiece tip may damage the eye's tissues, which is not desirable.

Figure 7:
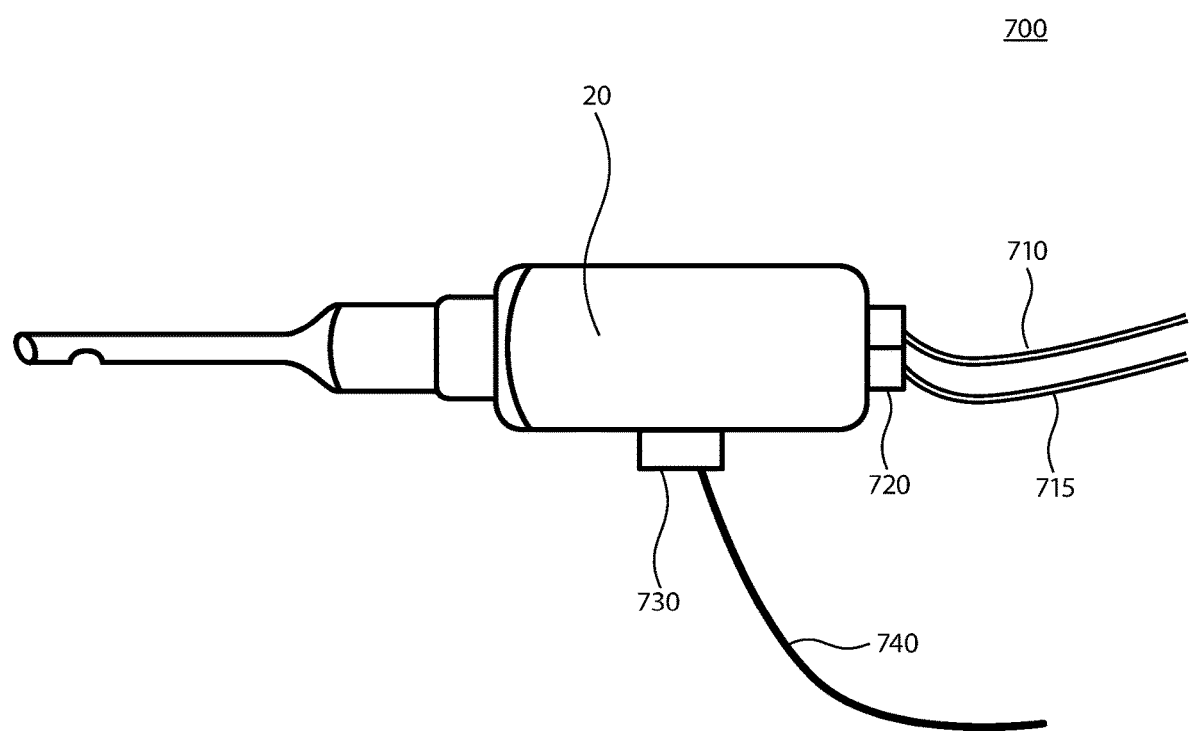
FIG. 7 illustrates an alternative aspect of the phacoemulsification/diathermy/vitrectomy system.

As illustrated in handpiece system 700 of FIG. 7, at least one sensor module 720 may be placed in proximity to the phacoemulsification handpiece. Such a module may include a pressure sensor in communication with irrigation line 710 as well as a pressure sensor in communication with the aspiration line 715. The sensor module 720 may receive power and transmit sensor measurement data over power and data pins located in the communication module 730 located on the handpiece 20. The communication module 730 may operate on a specific voltage, for example, and may transmit measurements to the console and or system via a wireless or wired connection.

As illustrated in FIG. 7, the module may receive power from the console or other aspect associated with the console through cable 740 and may similarly transmit data through cable 740. In an embodiment of the present invention, the handpiece system 700 may transmit sensor and other data wirelessly through communication module 730 via any known wireless communication means to a desired portion of the surgical console or system (not shown), such as, for example, via a dedicated wireless method such as Bluetooth Low Energy (BLE), Near Field Communications (NFC) or Wi-Fi technologies.

In an embodiment of the present invention, power to the phacoemulsification hand piece sensor module may be provided through a coin cell battery or like power source which may eliminate the need for cable 740. In such an embodiment, the lack of cable 740 may require the use of wireless communications through communication module 730, as discussed above, and may allow for a less cumbersome use of the handpiece 720. In an embodiment, communication module 730 may be part of sensor module 720.

A steady and inflated anterior eye chamber may allow the surgeon to perform a more successful phacoemulsification procedure for cataract lens extraction and IOL insertion than otherwise possible with a high variance of pressure in the anterior chamber of the patient's eye. The intraoperative pressure in the anterior chamber of the eye is a function of irrigation pressure, aspiration vacuum, and wound leakage. Variation of the anterior chamber pressure may come from the mismatch of sudden aspiration vacuum surge with unmet irrigation inflow, for example. The variation of the anterior chamber pressure causes instability and is not desirable during cataract lens extraction.

A typical method to provide a steady irrigation pressure is to hang a BSS bottle on an IV pole, or to pressurize the source BSS with additional pressure such as air or mechanical force, and connect the BSS via a tube to the irrigation port of the handpiece. The irrigation flow rate to the anterior chamber is then determined by the source pressure and the irrigation line resistance. The aspiration vacuum used may be generated by peristaltic pump or a Venturi vacuum source downstream from the handpiece aspiration port via a second tube. The aspiration vacuum level may be determined by the peristaltic vacuum setting, the Venturi vacuum setting, and/or one or more pressure or flow sensors. The aspiration vacuum may vary when operating in phacoemulsification mode when certain cataract material being removed from the anterior chamber partially or fully blocks the handpiece tip, also known as an occlusion event.

During an occlusion event, the vacuum continues to build up in the aspiration line, while the aspiration flow rate is reduced or stopped. Occasionally, the occlusion breaks free and the stored energy in the aspiration line is applied to the anterior chamber and suddenly pulls fluid from the anterior chamber resulting in a surge of outflow. When the irrigation inflow is substantially less than the aspiration out flow, the anterior chamber pressure will be less than steady state. More specifically, the anterior chamber pressure may be much lower than atmospheric pressure level, for example. Under such a condition, the anterior chamber may soften and become shallow, or in severe condition, may collapse.

In an embodiment of the present invention, methods for maintaining intraoperative IOP may include pressurized infusion, occlusion and post occlusion surge detection, and IOP control. More specifically, the present invention may utilize in-line irrigation and aspiration pressure sensors, as discussed above, to provide a more accurate and real-time measurement of system pressures nearer the surgical site. Such measurements, along with foot pedal position and bottle height (or specific irrigation pressure, for example), may provide inputs into certain algorithms (discussed in more detail herein) for control of system fractions.

For example, the present invention may increase infusion pressure (irrigation) or reduce the aspiration flow and/or vacuum upon the detection of a post occlusion surge event. Each of these aforementioned elements may be used to improve intraoperative IOP management throughout surgery. For example, using a pressurized irrigation source with the present invention may provide the capability of quickly increasing and/or decreasing irrigation pressure to maintain anterior chamber stability during post occlusion surge events, for example.

The present invention includes intraoperative pressure management algorithms which may incorporate at least some portion of measurable attributes associated with phacoemulsification surgery. Measurable attributes may include patient eye level and wound leakage calibration, intraocular pressure changes during aspiration outflow, occlusion and post occlusion surge detection and mitigation actions, balanced salt solution (BSS) usage, and irrigation and aspiration line block detection, for example.

Figure 8:
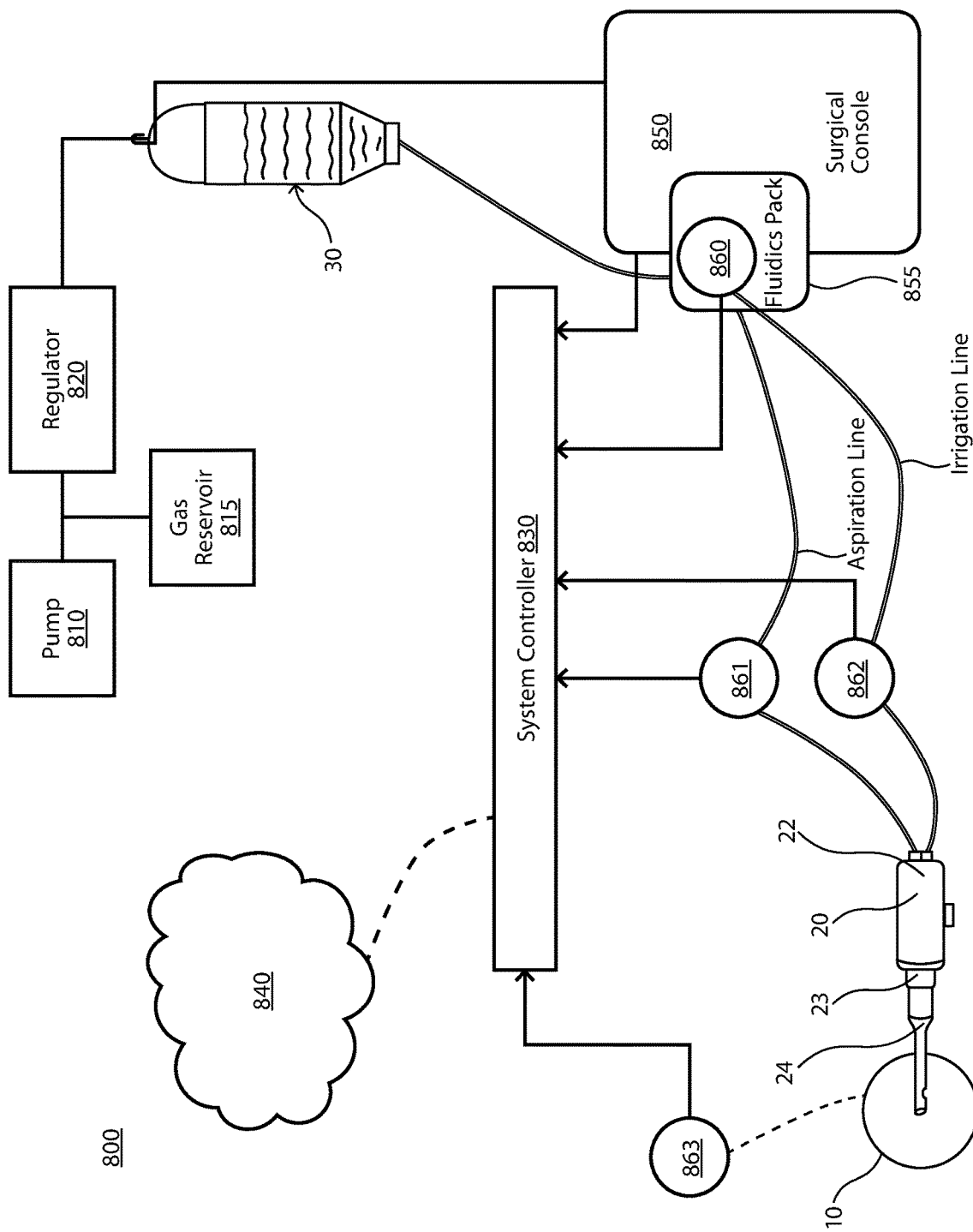
FIG. 8 illustrates an alternative phacoemulsification/diathermy/vitrectomy system and illustrated connected to various components of the system in order to determine characteristics or features of the components.

In an embodiment of the present invention, a plurality of pressure sensors may be used within a surgical system and may provide data which may be used to control aspects of the surgical system. A system level architecture and sensor placement of the present invention is illustrated in FIG. 8. In system 800, surgical console 850 may be in communication with irrigation source 30 and handpiece 20, for example. Surgical console 850 may also be in communication with pump 810, gas reservoir 815, and pressure regulator 820, each of which may be used for pressurized irrigation. Surgical console 850 may also be in communication with fluidics pack 855 and system controller 830, which may additionally be in communication with an intranet/internet 840.

Within system 800, an irrigation pressure sensor 862 may be located in close proximity to and/or be coupled to handpiece 20. Similarly, aspiration pressure/vacuum sensor 861 may be located in close proximity to and/or be coupled to handpiece 20. In an embodiment of the present invention, the aspiration pressure/vacuum sensor 861 may be used alone to provide substantially the same improvement in measurements. As described herein, the use of one or more pressure sensors may provide improved real-time measurements of patient eye level and wound leakage.

As used herein, "patient eye level" is defined as the height difference between the patient's eye and the fluidics pack where irrigation and aspiration lines are terminated. This height difference may result in a certain amount of pressure inside the anterior chamber. As would be understood by those skilled in the art, a handpiece with the appropriate tip/sleeve and irrigation/aspiration lines would be inserted in the patient's eye through an incision in the anterior chamber. "Wound leakage", as used herein, is defined as the fluid out flow from the anterior chamber during surgery through the incision site. The amount of fluid out flow and related pressure changes inside the chamber may be a function of incision size.

The irrigation pressure sensor 862 and aspiration pressure/vacuum sensor 861, may each be located at the handpiece 20 and may be able to measure the pressure changes inside the anterior chamber due to patient eye level and wound leakage given close proximity of the sensors to the anterior chamber. In an embodiment of the present invention, during the prime/tune of surgical console 850, the system 800 may perform an initial patient eye level calibration by storing pressure measurements taken by sensor 861 and sensor 862. Similarly, subsequent measurements may be taken by sensor 861 and sensor 862 and stored when the handpiece 20 is inserted into the anterior chamber while there is no aspiration out flow.

As will be appreciated by those skilled in the art, intraoperative pressure may change inside the anterior chamber during aspiration outflow. In an embodiment of the present invention, a surgeon may program surgical console 850 to establish a desired intraoperative pressure prior to the start of surgery. When handpiece 20 is inserted into the anterior chamber of the eye 10, the intraoperative pressure management algorithm may take one or more measurements from the irrigation pressure sensor 862, for example, and compare the obtained value to the desired pressure value contained in the console 850 and/or stored in system controller 830. If, for example, the irrigation pressure sensor 862 measurement is higher than the desired pressure, then the algorithm may reduce the irrigation pressure by commanding the pressure regulator 820 to vent excess pressure until the irrigation pressure is substantially equal to the desired pressure. If, for example, the irrigation pressure measurement is lower than the desired pressure, then the algorithm may increase the irrigation pressure by commanding the pressure regulator 820 to increase pressure until the irrigation pressure is substantially equal to the desired pressure.

Figure 9A:
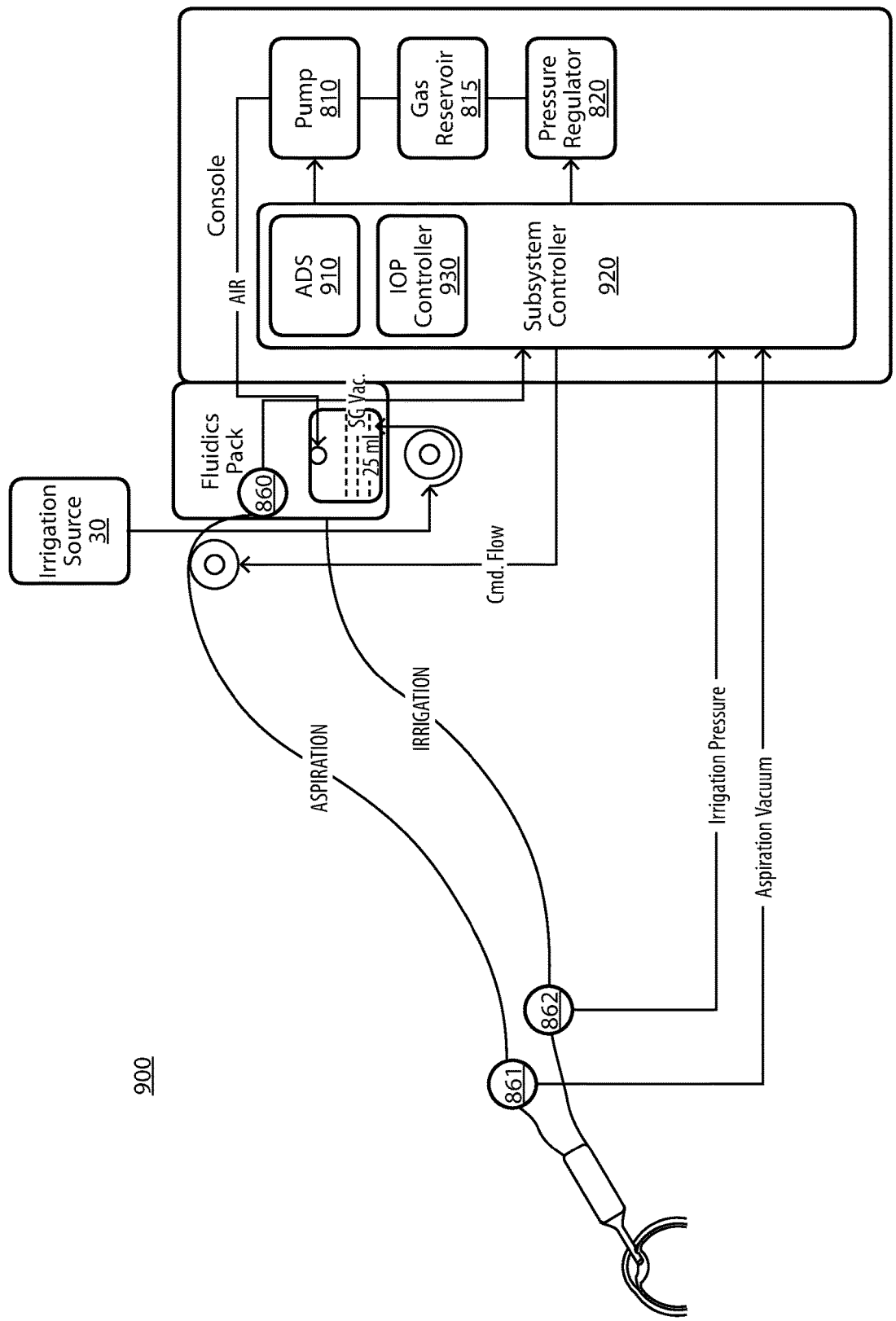
FIG. 9A illustrates an alternative phacoemulsification/diathermy/vitrectomy system and illustrated connected to various components of the system in order to determine characteristics or features of the components.
Figure 9B:
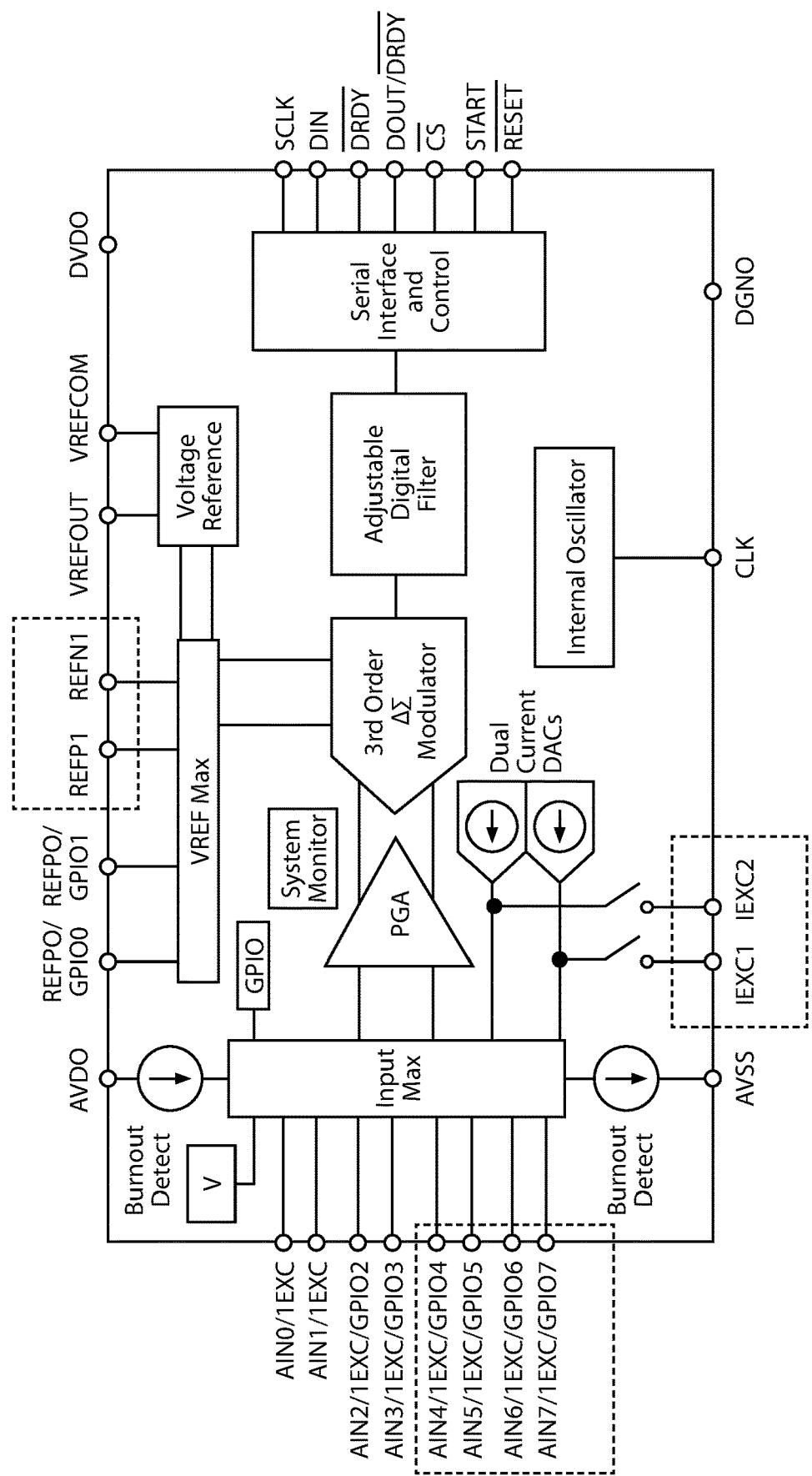
FIG. 9B illustrates circuitry associated with an embodiment of the present invention.

As illustrated in FIG. 9A, the intraoperative pressure management algorithm, which may be resident in surgical console 850, and, more particularly, within subsystem controller 920, may receive sensor data from the analog to digital converter (ADS) 910, and may continuously measure and adjust the irrigation pressure of system 800 through the IOP management controller 930, in order to maintain the anterior chamber pressure within certain intraoperative parameters. An exemplary ADS for use with system 900 is illustrated in FIG. 9B. By way of non-limiting example, the intraoperative pressure management algorithm my account for a drop in the anterior chamber pressure due to fluid out flow when the surgeon begins to aspirate fluid by pressing on a foot pedal controller (not shown). The IOP management controller 930 may control the pump 810, a gas reservoir 815, the pressure regulator 820, and the height of irrigation source 30.

In an embodiment of the present invention during peristaltic (flow) based aspiration, the intraoperative pressure management algorithm may obtain data related to the intraoperative pressure drop caused by the aspiration out flow from the console 850. Such data may be stored as a lookup table or as linear/polynomial functions of commanded aspiration flow rates (as provided to the console through operation by a surgeon during a procedure) and may take the form as shown below:

| Commanded Aspiration Flow Rate (ccm), CF(n) | Change in intraoperative pressure, ($\Delta$Pn) |
|---|---|
| $CF(n_0)$ | $\Delta P(n_0)$ |
| $CF(n_1)$ | $\Delta P(n_1)$ |
| $CF(n_2)$ | $\Delta P(n_2)$ |
| $CF(n_3)$ | $\Delta P(n_3)$ |
| $CF(n_4)$ | $\Delta P(n_4)$ |
| $CF(n_5)$ | $\Delta P(n_5)$ |
| $CF(n)$ | $\Delta P(n)$ |

The intraoperative pressure management algorithm may adjust the irrigation pressure via the IOP management controller 930 based on the commanded aspiration flow rate and respective change in the intraoperative pressure. For example:

Irrigation Pressure $(t)=$
  Irrigation Pressure $(t-1)+/-\Delta P(n)$

As illustrated in the equation above, the Irrigation Pressure (t–1) would be equal to the desired pressure set initially prior to aspiration outflow. For a given commanded aspiration outflow, the algorithm may increase or decrease the irrigation pressure based on the commanded aspiration flow rate in order to keep the anterior chamber pressure within desired pressure range during the surgery.

In Venturi (vacuum) based aspirations, for example, the intraoperative pressure management algorithm may obtain the intraoperative pressure drop caused by the aspiration out flow from console 850. This may be a lookup table or linear/polynomial function of actual Venturi vacuum measured by sensor 861 and represent respective changes in the intraoperative pressure inside the chamber as shown below:

| Measured Venturi Vacuum (mmHg), MV(n) | Change in intraoperative pressure, ($\Delta$Pn) |
|---|---|
| $MV(n_0)$ | $\Delta P(n_0)$ |
| $MV(n_1)$ | $\Delta P(n_1)$ |
| $MV(n_2)$ | $\Delta P(n_2)$ |
| $MV(n_3)$ | $\Delta P(n_3)$ |
| $MV(n_4)$ | $\Delta P(n_4)$ |
| $MV(n_5)$ | $\Delta P(n_5)$ |
| $MV(n)$ | $\Delta P(n)$ |

Similarly, the intraoperative pressure management algorithm may adjust the irrigation pressure to the handpiece 20 based on the measured Venturi vacuum and respective change in the intraoperative pressure.

Irrigation Pressure $(t)=$
  Irrigation Pressure $(t-1)+/-\Delta P(n)$

The Irrigation Pressure (t–1) would be equal to desired pressure set initially prior to aspiration outflow. With the aspiration outflow, the algorithm would increase or decrease the irrigation pressure based on the measured Venturi vacuum in order to keep the anterior chamber pressure within the desired pressure range during the surgery. The intraoperative pressure management algorithm may also continue to monitor if the aspiration flow is increasing or decreasing or has become at least partially occluded and may adjust the irrigation pressure accordingly.

In an embodiment of the present invention, the intraoperative pressure management algorithm may measure the difference between sensor 861 and sensor 860 along the aspiration fluid path to calculate actual aspiration flow rate in real-time. This method may be used for both Peristaltic and Venturi based aspiration. The fluid flow between two points of measurement along the aspiration line with a known radius and length may be directly related to pressure difference. Thus, an increase in fluid flow may result in a higher pressure difference between two points and vice versa. Similarly, if the aspiration line is fully or at least partially occluded the pressure difference between two points may approach zero. Using the Hagen-Poiseuille law of fluid dynamics:

$$\Delta P = \frac{8\mu L Q}{\pi r^4}$$

Wherein $\Delta P$=Average (sensor 861)–Average (sensor 860); r=inner radius of the aspiration tubing; L=length of aspiration tubing from sensor 860 to sensor 861; Q=flow rate of the fluid (i.e., water or BSS); and $\mu$=viscosity of the fluid (i.e., water or BSS).

As previously described, the algorithm may use a lookup table or linear/polynomial function of actual or measured aspiration flow rate and respective change in the intraoperative pressure inside the chamber as shown below:

| Actual or Measured Aspiration Flow Rate (ccm), MF(n) | Change in intraoperative pressure ($\Delta$Pn) |
|---|---|
| $MF(n_0)$ | $\Delta P(n_0)$ |
| $MF(n_1)$ | $\Delta P(n_1)$ |
| $MF(n_2)$ | $\Delta P(n_2)$ |
| $MF(n_3)$ | $\Delta P(n_3)$ |
| $MF(n_4)$ | $\Delta P(n_4)$ |
| $MF(n_5)$ | $\Delta P(n_5)$ |
| $MF(n)$ | $\Delta P(n)$ |

The intraoperative pressure management algorithm may adjust the irrigation pressure based on the actual aspiration flow rate and respective change in the intraoperative pressure. Again:

Irrigation Pressure $(t)=$
Irrigation Pressure $(t-1)+/-\Delta P(n)$

Where the Irrigation Pressure (t-1) would be equal to desired pressure set initially prior to aspiration outflow. With the aspiration outflow, the algorithm may increase or decrease the irrigation pressure based on the actual aspiration flow rate in order to keep the anterior chamber pressure within desired pressure range during the surgery.

In an embodiment of the present invention, the intraoperative pressure management algorithm may measure the difference between the two aspiration pressure/vacuum/flow sensors 860 and 861 along the aspiration fluid path to determine the change in intraoperative pressure due to the aspiration outflow. This method may be the same for both peristaltic and Venturi based aspiration. The fluid flow between two points of measurement along the line with certain radius and length is directly related to pressure difference. Thus, an increase in fluid flow may result in a higher pressure difference between two points and vice versa. When the aspiration line is partially to fully occluded (i.e., restricted to no fluid flow), the pressure difference between two points would approach zero. Again, the algorithm may rely on a lookup table or linear/polynomial function of aspiration pressure/vacuum difference and the respective change in the intraoperative pressure inside the chamber as shown below:

| Change in Aspiration line pressure/vacuum (Average (sensor 861) − Average (sensor 860)), $\Delta MV(n)$ | Change in intraoperative pressure, $\Delta P(n)$ |
|---|---|
| $\Delta MV(n_0)$ | $\Delta P(n_0)$ |
| $\Delta MV(n_1)$ | $\Delta P(n_1)$ |
| $\Delta MV(n_2)$ | $\Delta P(n_2)$ |
| $\Delta MV(n_3)$ | $\Delta P(n_3)$ |
| $\Delta MV(n_4)$ | $\Delta P(n_4)$ |
| $\Delta MV(n_5)$ | $\Delta P(n_5)$ |
| $\Delta MV(n)$ | $\Delta P(n)$ |

The intraoperative pressure management algorithm may adjust the irrigation pressure based on the actual aspiration flow rate and respective change in the intraoperative pressure. Again, using:

Irrigation Pressure $(t)=$
Irrigation Pressure $(t-1)+/-\Delta P(n)$

Where the Irrigation Pressure (t-1) would be equal to desired pressure set initially prior to aspiration outflow. With the aspiration outflow, the algorithm may increase or decrease the irrigation pressure based on the actual aspiration flow rate in order to keep the anterior chamber pressure within desired pressure range during the surgery. As discussed herein, the intraoperative pressure management algorithm may continue to monitor if the aspiration flow has increased or decreased or has become partially or fully occluded, and may adjust the irrigation pressure accordingly. Other inputs to the algorithm, such as foot pedal console control, such as transitioning between known positions of commands, may be used in combination with actual flow measurements to keep the anterior chamber pressure stable during the aspiration flow.

In an embodiment of the present invention, occlusion and post occlusion surge detection and mitigation may be obtained through the use of pressure sensors proximate to the surgical site, preferably on the distal end of the handpiece. As discussed above, occlusion and post occlusion surge detection may be detected in both peristaltic and Venturi based aspiration. By way of example, during aspiration outflow, an occlusion may be created when the handpiece tip is blocked by small fragment of cataract particulate. The blocked tip may cause a vacuum to build in the aspiration line. If the occlusion breaks, the stored the stored energy in the tubing pulls fluid from the anterior chamber. The volume of fluid that the aspiration tubing pulls depends on how much the tubing deformed during the occlusion. This deformation in conjunction with the occlusion itself causes a post occlusion surge in the aspiration line and a drop in intraoperative pressure inside the anterior chamber of the patient's eye.

The algorithm uses the sensors 860 and 861 to detect tip occlusions and post occlusion surge using:

Pressure Surge=sensor $861(t)$−sensor $860(t-1)$.

The algorithm may detect tip occlusions if, for example, the pressure surge is greater than a predetermined occlusion threshold and the current sensor 860 measurement is greater than 90% of maximum set vacuum in both Peristaltic and Venturi based aspiration.

Irrigation Pressure (t) would be set to desired intraoperative pressure established by a user of the phacoemulsification system earlier or prior to the start of surgery. The algorithm may then help detect post occlusion surge if the pressure surge is greater than predetermined post occlusion surge threshold in both peristaltic and/or Venturi based aspiration.

Irrigation Pressure (t) would be set based on the aspiration outflow established earlier or prior to the start of surgery.

Figure 10A:
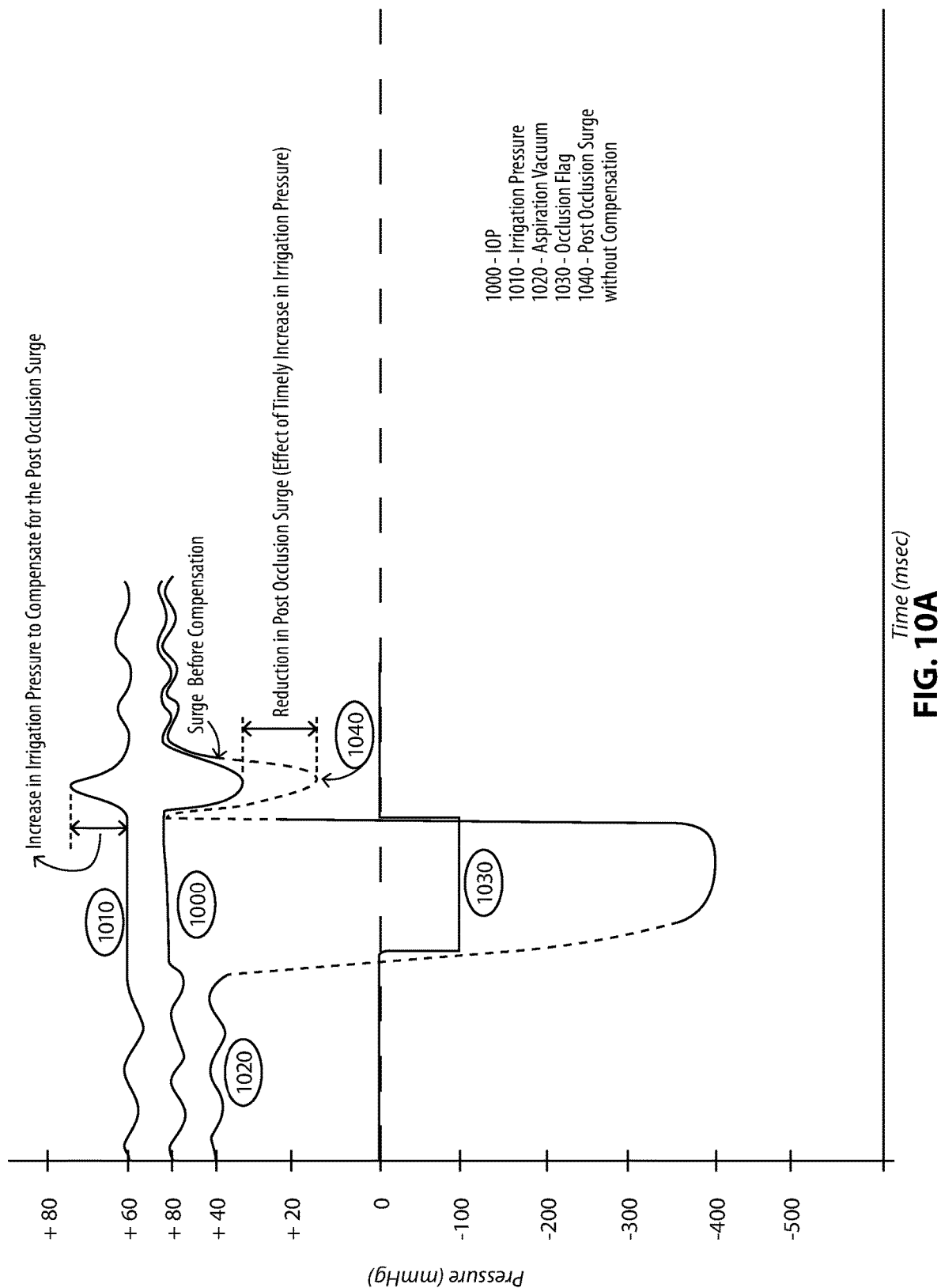
FIG. 10A illustrates pressure data associated with an embodiment of the present invention.
Figure 10B:
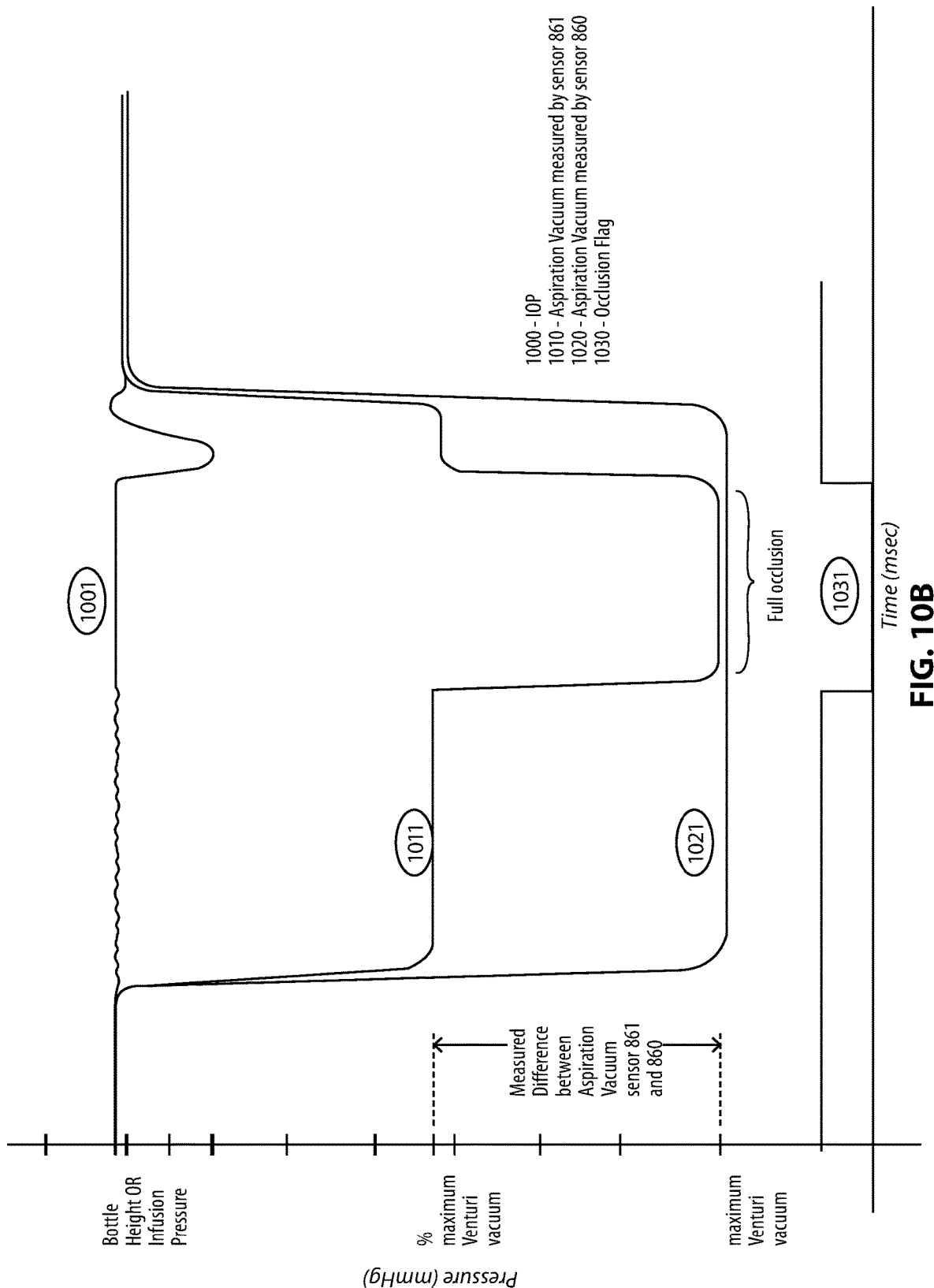
FIG. 10B illustrates pressure data associated with an embodiment of the present invention.

Both Peristaltic and Venturi based aspiration system using the intraoperative pressure management algorithm has the capability to at least partially mitigate the effects of post occlusion surge by providing the timely addition of infusion flow to compensate for fluid loss during a surge event. In FIG. 10A, for example, the actual IOP measured is indicated by line 1000, the actual measured irrigation pressure is indicated line 1010, the actual measured aspiration vacuum is measured by line 1020, and the system generated flag indicative of an occlusion event is line 1030. As is illustrated in FIG. 10A, for example, a sudden and steep increase in the aspiration vacuum may be indicative of an occlusion event. Similarly, as illustrated in FIG. 10B, the difference between sensors, for example sensor 861 and sensor 860, may be calculated as a percentage of a maximum ventri vacuum. As the actual IOP is measured as indicated by line 1001, the actual measured irrigation pressure is indicated line 1011 may be compared against the actual measured aspiration vacuum as measured by line 1021. As illustrated, as the plot lines for each of the sensors converge towards each other, a near-full or full occlusion may be assumed. A near-full or full occlusion may generate a flag, as illustrated in time by line 1031, which may allow the system or system operator.

The present invention may use the algorithm discussed herewith to begin ramping up the irrigation pressure with determined slope when, for example, a tip occlusion has occurred and is detected. For example, irrigation pressure as measured by sensor 862, in FIG. 9A, proximate to the distal end of the handpiece 20 may be close to column height of the fluid or specified infusion pressure after accounting for patient eye level and wound leakage in a continuous irrigation or irrigation only mode. During surgery, if an occlusion at the tip of the handpiece 20 occurs, aspiration flow may be stopped or slowed depending on the type of occlusion which may, in turn, cause the aspiration vacuum to reach maximum present vacuum and the irrigation flow to stop or slow and irrigation pressure to increase to column height of the fluid or specified infusion pressure. This information may allow the algorithm to detect an occlusion, which, when removed, may allow the aspiration flow to be restored to the preset maximum aspiration flow rate. This rapid change in aspiration flow may trigger a post occlusion surge event inside the anterior chamber of the eye and may lead to a quick decrease in irrigation pressure and a decrease in aspiration vacuum. Upon detection of a post occlusion surge event, the present invention may increase the infusion pressure in time to substantially make up for the lost fluid volume due to aspiration flow. This may reduce the effect of the post occlusion surge inside the anterior chamber and keep the chamber at equilibrium.

Figure 11:
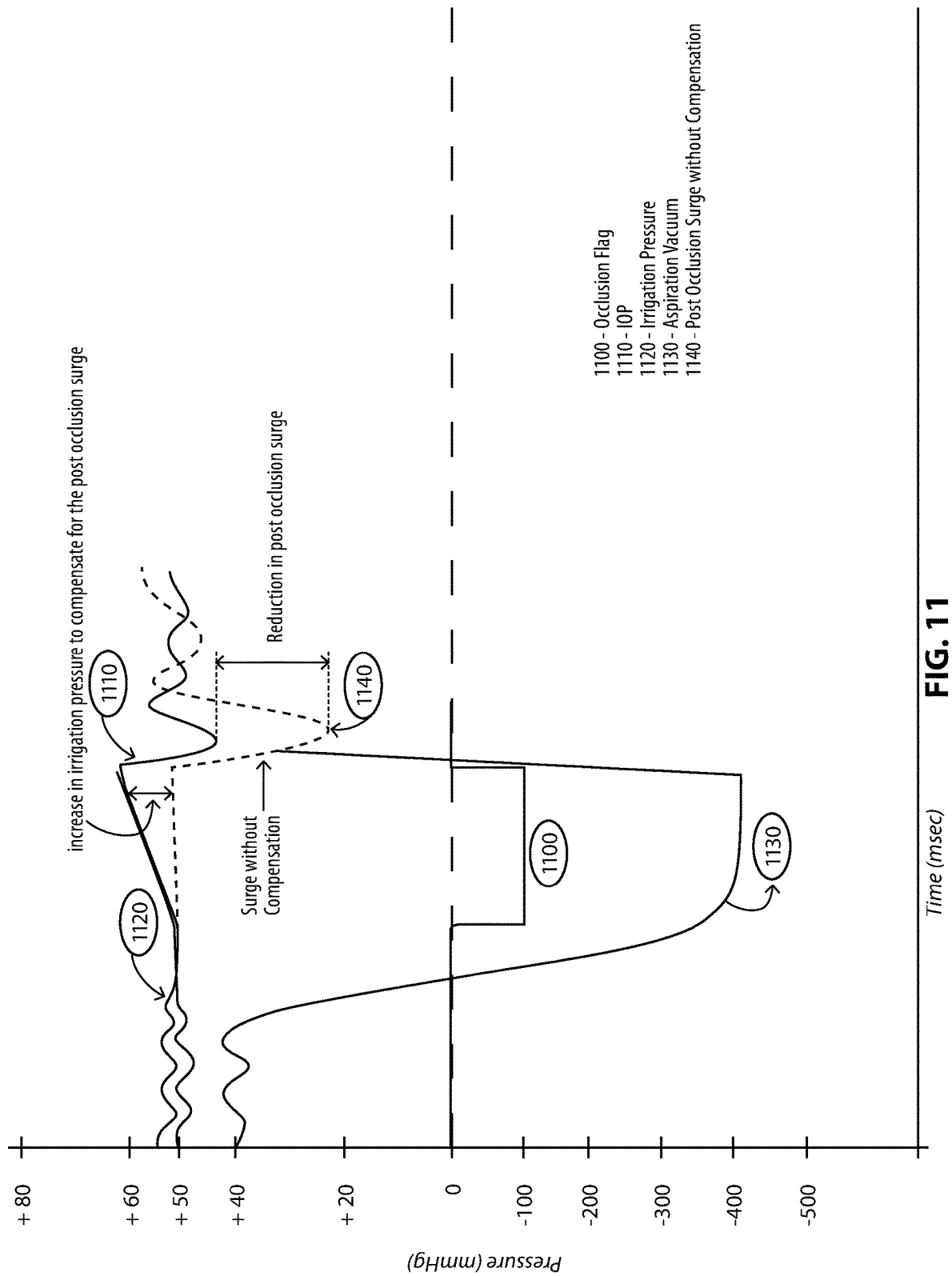
FIG. 11 illustrates pressure data associated with an embodiment of the present invention.

As illustrated in FIG. 11, a peristaltic system may behave in a similar manner under the control of the present invention. The algorithm of the present invention may detect that an occlusion has occurred as indicated by the occlusion flag line 1100 going low with the post occlusion surge event approaching as indicated by the occlusion flag line 1100 going high. When the occlusion flag line 1100 goes low, the present invention may begin to increase the infusion pressure with a certain slope and maintain the a pressure at a certain level once it reaches an upper bound of about 100 mmHg, for example. When the post occlusion surge event occurs, additional infusion pressure, illustrated by irrigation line 1120, may help to reduce the effect of a surge event, as illustrated by aspiration line 1130, as shown in the IOP line 1110 staying above about 20 mmHg. The increase in infusion pressure may be a function of aspiration vacuum such that a higher aspiration vacuum may lead to quicker infusion pressure build up.

The infusion pressure may be limited to a certain upper bound to ensure that pressure is within acceptable range—an upper bound which may be set by the user of the system. When the occlusion break occurs, the addition infusion flow may help to reduce the drop in the intraoperative pressure, thus providing greater anterior chamber stability:

As would be appreciated by those skilled in the art, the intraoperative pressure management algorithm of the present invention may provide a capability to determine BSS usage during the surgery. The system may use a peristaltic pump to transfer fluid from the BSS bottle or bag to the pressurized infusion tank inside the fluid pack 855, as illustrated in FIG. 8. The present invention, via the console 850, for example, may track the starting and ending encoder counts to determine the amount of fluid transferred to the tank. A running count may be accumulated throughout the surgery to provide real-time BSS usage. The BSS usage may be reset when the fluid pack 855 is ejected from the system.

Figure 12:
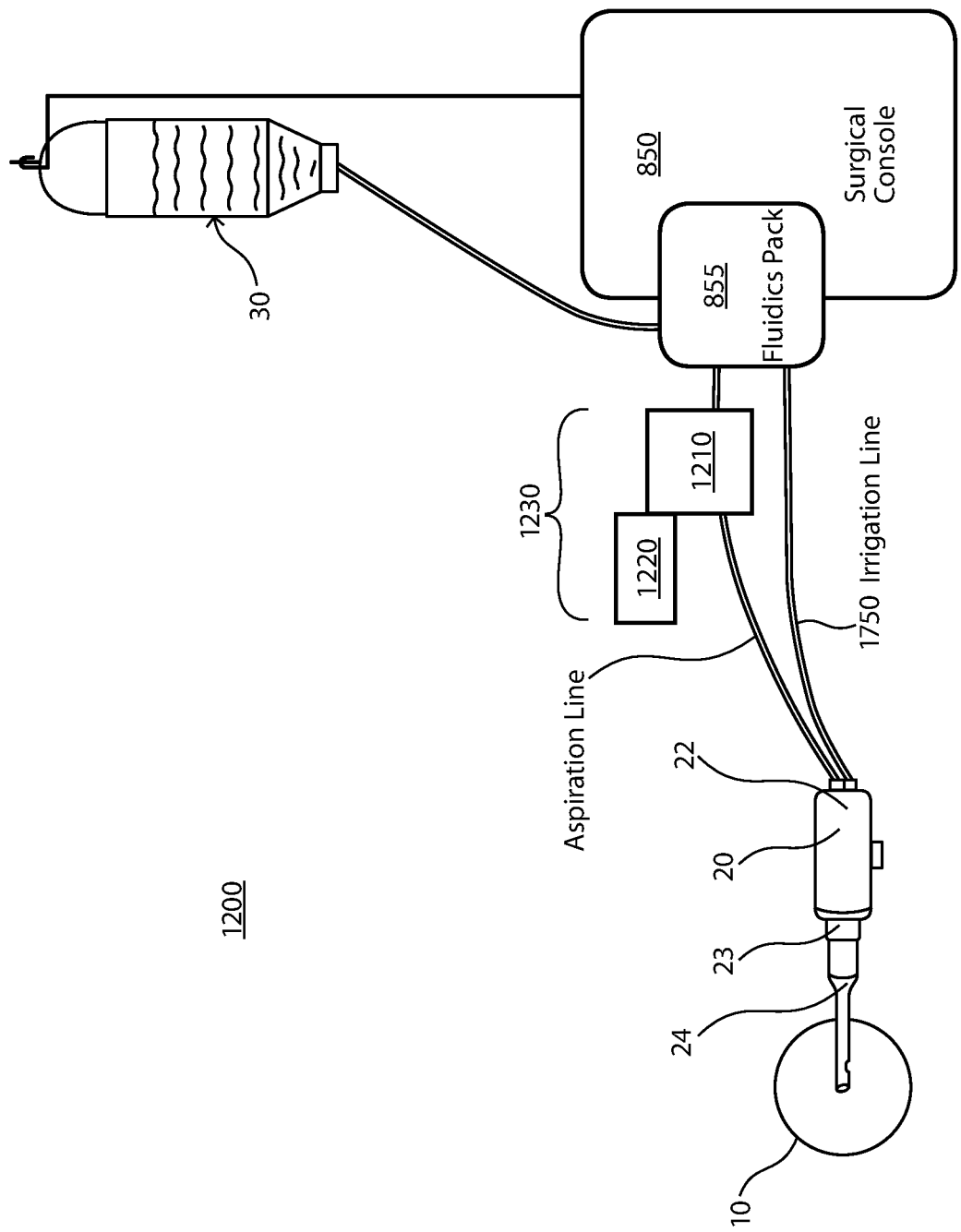
FIG. 12 illustrates an alternative phacoemulsification/diathermy/vitrectomy system and illustrated connected to various components of the system in order to determine characteristics or features of the components.

As illustrated in FIG. 9 and as above, ADS 910, for example, may be programmed to perform at least one function when an occlusion has been detected and/or an occlusion threshold has been met or exceeded. As illustrated in FIG. 12, the ADS 910 may monitor for an occlusion flag which may be true if the algorithm detects a post occlusion surge, for example. If true, the infusion pressure of the system may be measured and if a threshold is not met, which threshold may be set by the user of the system, the system may provide incremental infusion pressure based on the algorithm of the present invention.

Figure 13:
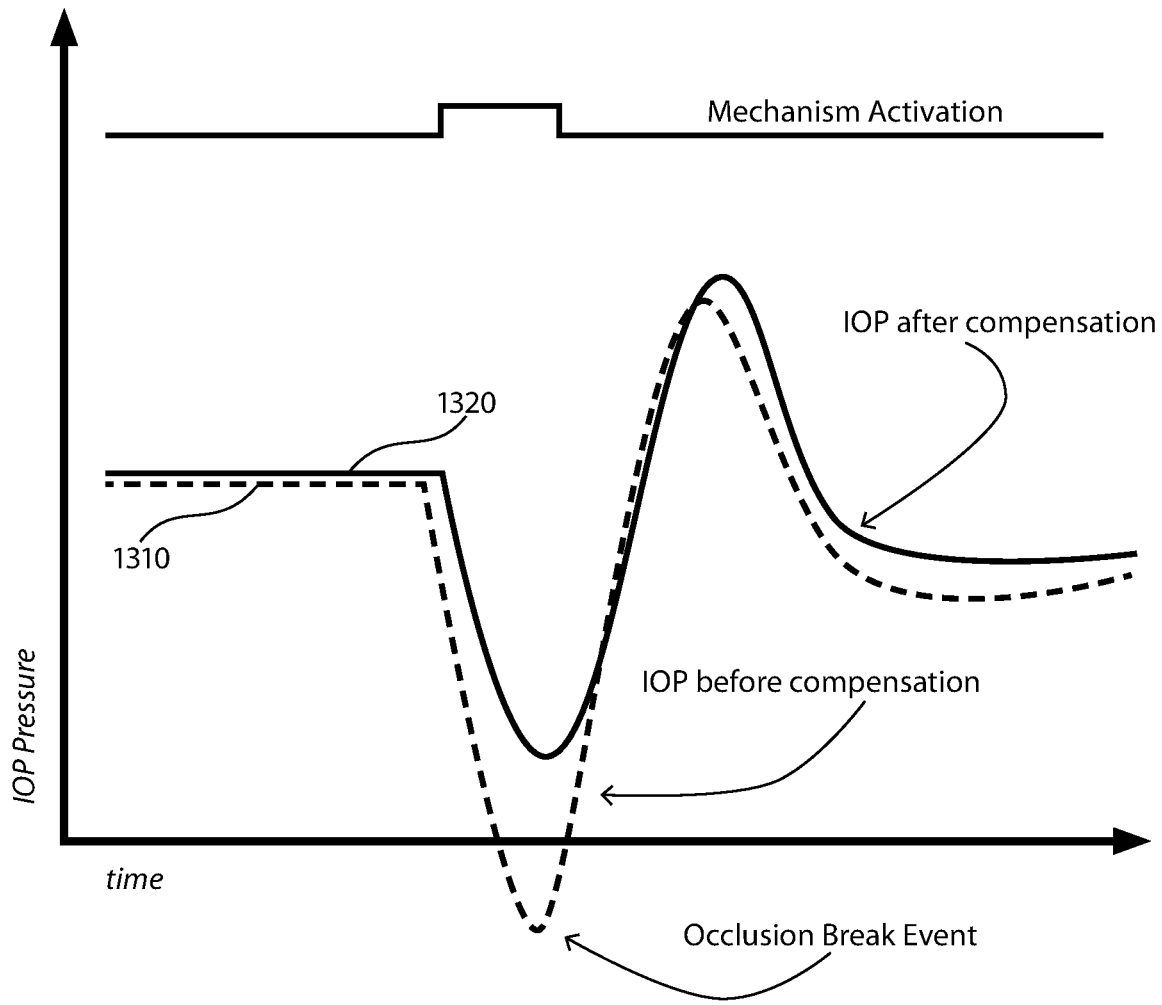
FIG. 13 is a chart illustrative of an embodiment of the present invention.

Similarly, and to prevent errors in pressure control within the system, the present invention may measure system irrigation pressure as illustrated in FIG. 13, for example. As with all programming associated with the surgical console, given the communicative nature of the various microchip inclusive components within the surgical console and those remotely based but in communication with the surgical console, the processing of commands and/or data collected or detected by the system may occur wherever one skilled in the art deems more efficient and/or suitable. As illustrated in FIG. 13, for example, the system may provide an alert to a user of the system that the irrigation within the system has been interrupted.

As discussed herein throughout, and as illustrated in FIG. 14, the algorithm of the present invention may be used with system usage based on peristaltic or Venturi based modes. For example, whether or not an occlusion is determined to be occurring, the present invention, as illustrated in FIG. 14, may balance a targeted infusion pressure with a desired IOP. As would be known to those skilled in the art, peristaltic vacuums may be created by using rollers to compress the aspiration line in a peristaltic manner, thereby creating constant flow and vacuum when the phacoemulsification tip is at least partially occluded. On the other hand, a Venturi vacuum is created by the flow of a fluid, typically air, over an opening utilizing the Venturi effect. An advantage of a Venturi pump is that it is able to create a preset vacuum level without occlusion of the phacoemulsification needle tip. For example, when the surgeon depresses the foot pedal, preset vacuum level may immediately be created.

In an embodiment of the parent invention, the existence of an occlusion may be determined by the system by first measuring and storing values of system aspiration and irrigation to use as a benchmark against additional measurements taken during system use. Benchmarks which may be compared to real time system measurements and used with the IOP prediction algorithms discussed hereinabove. If an occlusion is detected, the present invention may utilize the post occlusion management algorithm and may continue to loop through until no occlusion and, thus, no post occlusion surge, is detected.

The present invention may also determine if either the irrigation and/or aspiration line has been disconnected to either the handpiece or surgical console. The intraoperative pressure management algorithm may be used to monitor each of the in-line sensors associated with the system and alert the user if, for example, open atmosphere pressure is detected.

In an embodiment of the present invention, both irrigation and aspiration pressure sensors may be placed away from the handpiece. However, propagation delay caused by the tubing length and other characteristics would need to be added into the algorithm. In an embodiment of the present invention, both irrigation and aspiration sensors may be placed inside the fluidics pack to measure the irrigation and/or aspiration pressure during surgery. In an embodiment of the present invention, in-line or non-contact flow sensors may be used to measure the irrigation and/or aspiration flow during surgery. The intraoperative pressure management algorithm may be modified to incorporate data associated with fluid flow changes during surgery.

In an embodiment of the present invention, at least two in-line aspiration pressure sensors may be used to measure the pressure difference along the aspiration fluid path. A first sensor may reside inside the surgical console (e.g., a strain gauge vacuum) and a second sensor may be placed at the distal end of the handpiece on the aspiration luer connector, for example. These two sensors may measure the aspiration pressure/vacuum real-time during the surgery. The fluid flow between these two points of measurement along a tube having a certain radius and length is directly related to pressure difference. Thus, an increase in fluid flow would result in higher pressure difference between two points and vice versa. As discussed above, when the aspiration line is partially or fully occluded (i.e., near to no fluid flow), the pressure difference between the two sensors would approach zero. The use of the present invention may allow for real-time Venturi aspiration flow determination which may allow the flow to be adjusted as necessary to maintain a stable anterior chamber of the eye during surgery.

In an embodiment of the present invention, a mass air flow sensor may be placed in-line between the Venturi source/regulator and the Venturi output port on the fluid pack manifold. The Venturi fluid flow may be established based on the Venturi air flow changes detected by the mass air flow sensor.

As discussed above, maintaining anterior chamber pressure is of high value to both the patient and the surgeon alike. In an embodiment of the present invention, to maintain anterior chamber pressure in a near-steady state, or at least to keep the anterior pressure within a safe margin above atmospheric pressure, the aspiration flow rate may be limited by using a small inside diameter aspiration line and phacoemulsification tip, or to set the vacuum limit to a lower value. Similarly, the irrigation line flow capability may be increased by raising the irrigation pressure, or increasing the inside diameter of the irrigation line. However, over reducing the inside diameter of the aspiration line and the phacoemulsification tip may cause clogging during phacoemulsification, and may reduce the aspiration vacuum limit which may greatly impact the efficiency of the phacoemulsification procedure. Similarly, raising the IV pole height or otherwise increasing the irrigation pressure may effectively increase irrigation pressure, but such pressure increases may to too long to effectuate. For example, such methods raise pressure at best in a matter of ¹⁄₁₀ of a second, or seconds. Furthermore, increasing the inside diameter of the irrigation line may making priming more difficult.

In an embodiment of the present invention, the system may automatically provide momentary additional irrigation fluid pressure when an occlusion occurs and during an occlusion break by using a mechanism to apply force (pressure) on at least a section of the irrigation path which may contain enough fluid to compensate for the fluid loss experienced in the anterior chamber of the eye during an occlusion break. For example, when the system detects the event of occlusion or occlusion break, a reduced pressure mechanism may apply a pressure to this section in the irrigation path, causing this section to deform, thus momentarily forcing additional irrigation fluid to be supplied to the anterior chamber to compensate for the sudden fluid outflow caused by occlusion break. The applied pressure to the tubing section is intended to generate a momentary fluid pressure, and not to cut off the irrigation flow. In an embodiment of the present invention, the response time of applying the burst of fluid pressure in the irrigation line may be faster than, for example, raising the pressure in the irrigation line by raising the height of the irrigation source and/or adding gas pressure to the irrigation source.

As illustrated in FIG. 12, the reduced pressure mechanism 1230 may be located at any point along irrigation line 1250 between the irrigation source 30 and the handpiece 20. An in-line check valve (not shown) in series and between reduced pressure mechanism 1230 and irrigation source 30 may ensure that pressured fluid moves towards the handpiece 20 and may also prevent fluid back flow from the anterior chamber toward the irrigation source 30 when the mechanism retracts from the activated position to deactivated position, for example. Reduced pressure mechanism 1230 may be a single, unitary device, such as a direct action actuator which may exert pressure on the irrigation line 1250 by using a plunger or other like apparatus to reduce the interior diameter of the irrigation line 1250 sufficiently to force a quantity of irrigation fluid forward through the handpiece 20 into the eye 10. As discussed above, sensors associated with the present invention may allow the surgical console 850 to track and monitor pressure changes associated with occlusions and may activate reduce pressure mechanism 1230 as necessary to maintain a desired pressure in the eye 10, and, more specifically, in the anterior chamber of eye 10.

Reduced pressure mechanism 1230 may also be composed of multiple parts. For example, reduced pressure mechanism 1230 may include an actuation mechanism 1220 and a compensation volume module 1210. The inclusion of a compensation volume module 1210 may allow for an increased volume of irrigation fluid available to the reduced pressure mechanism 1230. For example, compensation volume module 1210 may include additional amounts of irrigation line 1250 which may be acted upon by actuation mechanism 1220. Such an increased amount of line may be accommodated by looping the line in a circular pattern and/or weaving the line in a serpentine manner. In any embodiment of line aggregation, those skilled in the art will recognize the various adaptations of actuators and plunger like formations may be made suitable to in part a desired force on at least a portion of the aggregated irrigation line. Similarly, in an embodiment of the present invention, compensation volume module 1210 may include a reservoir of irrigation fluid which may be introduced into irrigation line 1250 as necessary to create or augment an increase in pressure. In an embodiment of the present invention, the reduced pressure mechanism 1230 and/or in-line check valve 1240 may be incorporated into fluid pack 855. In an embodiment of the present invention, fluid pack 855 may be in the form of a cassette which may be removably attached to surgical console 850 and may include at least one reduced pressure mechanism 1230 and/or at least one in-line check valve 1240.

In an embodiment of the present invention, the amount of momentary fluid pressure and the duration of time the applying time of the irrigation source may be adjusted by the reduced pressure mechanism 1230 with the amount of pressure and time related to the compensation volume and the speed of the mechanism. As illustrated in FIG. 13, the activation of reduced pressure mechanism 1230 may lessen the drop in pressure experienced by a partial or full occlusion during phacoemulsification surgery. The graph illustrated in FIG. 13 shows a steep negative change in system pressure sans activation of reduced pressure mechanism 1230 as illustrated by the dashed line. The solid line illustrated in FIG. 13 illustrates system pressure with activation of the reduced pressure mechanism 1230.

More specifically, the activation of the reduced pressure mechanism 1230 may correspond to the detection of the occlusion event by the system and may be deactivated proximate to an indication that the irrigation pressure of the system is recovering. The increased pressure applied by the reduced pressure mechanism 1230 significantly reduces the loss of pressure due to an occlusion event and, used alone, may not affect the increase in pressure that might be experienced by the system after compensation for the occlusion event. In an embodiment of the present invention, the use of the reduced pressure mechanism 1230 may be included with other aspects of the present invention to improve the reduction in pressure loss and to mitigate any undesired pressure gain after compensation for an occlusion event.

The previous description is provided to enable any person skilled in the art to make or use the disclosed embodiments. Various modifications to these embodiments will be readily apparent to those skilled in the art, and the generic principles defined herein may be applied to other embodiments without departing from the spirit or scope of the invention. Thus, the present disclosure is not intended to be limited to the embodiments shown herein but is to be accorded the widest scope consistent with the principles and novel features disclosed herein.

What is claimed is:

1. A system for varying pressure rates during phacoemulsification surgery, the system comprising:
   a surgical console having at least one system bus communicatively connected to at least one computing processor capable of accessing at least one computing memory associated with the at least one computing processor;
   a phacoemulsification surgical handpiece having at least one surgical tool at a distal end of the phacoemulsification surgical handpiece;
   a first pressure sensor communicatively connected to an aspiration line and proximate to a proximal end of the phacoemulsification surgical handpiece and exterior to the surgical console; and
   a second pressure sensor communicatively connected to the aspiration line and proximate to a vacuum source associated with the surgical console and exterior to the phacoemulsification surgical handpiece,
   wherein the pressure of the aspiration line is regulated in accordance with a comparison between an estimated aspiration flow calculated from the pressure measured by the first and second pressure sensors communicatively connected to the aspiration line and a predetermined aspiration pressure.

2. The system of claim 1, wherein the estimated aspiration flow is calculated using the Hagen-Poiseuille equation.

3. The system of claim 1, wherein the first pressure sensor is in line with the aspiration line and the at least one surgical tool.

4. The system of claim 1, wherein the second pressure sensor is in line with the aspiration line and the vacuum source.

5. The system of claim 1, wherein the second pressure sensor is a strain gauge vacuum sensor.

6. The system of claim 1, wherein the first pressure sensor is located proximate to an aspiration luer connector.

7. The system of claim 1, wherein the first pressure sensor is communicatively connected to the at least one system bus.

8. The system of claim 1, wherein the second pressure sensor is communicatively connected to the at least one system bus.

9. The system of claim 1, further comprising a graphical user interface for receiving a visual indication of the estimated aspiration flow.

10. The system of claim 1, wherein the pressure of the aspiration line is raised to meet the predetermined aspiration pressure.

11. The system of claim 1, wherein the surgical tool comprises a phaco tip or needle.

12. A system for varying irrigation rates during phacoemulsification surgery, the system comprising:
    a surgical console having at least one system bus communicatively connected to at least one computing processor capable of accessing at least one computing memory associated with the at least one computing processor;
    a phacoemulsification surgical handpiece having at a distal end at least one surgical tool and having near a proximal end a detachable receiver for receiving an aspiration line and an irrigation line from the surgical console;
    a first pressure sensor communicatively connected to the aspiration line and located proximate to the detachable receiver and exterior to the surgical console; and
    a second pressure sensor communicatively connected to the aspiration line and proximate to a vacuum source associated with the surgical console and exterior to the phacoemulsification surgical handpiece,
    wherein the pressure of the irrigation line is regulated in accordance with an estimated aspiration flow calculated from the pressure measured by the first and second pressure sensors communicatively connected to the aspiration line.

13. The system of claim 12, wherein the estimated aspiration flow is calculated using the Hagen-Poiseuille equation.

14. The system of claim 12, wherein the first pressure sensor is in the line with the aspiration line and the at least one surgical tool.

15. The system of claim 12, wherein the second pressure sensor is in line with the aspiration line and the vacuum source.

16. The system of claim 12, wherein the second pressure sensor is a strain gauge vacuum sensor.

17. The system of claim 12, wherein the first pressure sensor is communicatively connected to the at least one system bus.

18. The system of claim 12, wherein the second pressure sensor is communicatively connected to the at least one system bus.

19. The system of claim 12, further comprising a graphical user interface for receiving a visual indication of the estimated aspiration flow.

20. The system of claim 12, further comprising a graphical user interface for receiving a visual indication of the pressure of the irrigation line.

21. The system of claim 12, further comprising a graphical user interface for receiving a visual indication of a measured flow of the irrigation line.

22. The system of claim 12, wherein the irrigation line is in communication with an irrigation source.

23. The system of claim 12, wherein the irrigation line is in communication with a pressurized irrigation source.

24. The system of claim 12, wherein the flow rate of the irrigation line is raised in accordance with the difference between the predetermined aspiration pressure and the estimated aspiration flow.

25. The system of claim 12, wherein the at least one surgical tool comprises a phaco tip or needle.

26. A system for varying pressure rates during phacoemulsification surgery, the system comprising:
    a surgical console having at least one system bus communicatively connected to at least one computing processor capable of accessing at least one computing memory associated with the at least one computing processor;
    a phacoemulsification surgical handpiece having at a distal end at least one surgical tool and having near a proximal end a mass air flow sensor communicatively connected to an aspiration line at a location exterior to the surgical console; and wherein the pressure of the aspiration line is regulated in accordance with a comparison between an estimated aspiration flow calculated from the pressure measured by the mass air flow sensor at the proximal end of the phacoemulsification surgical handpiece and a predetermined aspiration pressure.

\* \* \* \* \*